United States Patent
Trautman et al.

(10) Patent No.: US 8,821,446 B2
(45) Date of Patent: Sep. 2, 2014

(54) APPLICATORS FOR MICRONEEDLES

(75) Inventors: Joseph C. Trautman, Sunnyvale, CA (US); Robert Wade Worsham, Cupertino, CA (US); Danir F. Bayramov, Sunnyvale, CA (US); Danny Lee Bowers, Lake Odessa, MI (US); Steven Richard Klemm, Grand Rapids, MI (US); Parminder Singh, Union City, CA (US)

(73) Assignee: Corium International, Inc., Menlo Park, CA (US)

( * ) Notice: Subject to any disclaimer, the term of this patent is extended or adjusted under 35 U.S.C. 154(b) by 0 days.

(21) Appl. No.: 12/009,954

(22) Filed: Jan. 22, 2008

(65) Prior Publication Data
US 2008/0183144 A1 Jul. 31, 2008

Related U.S. Application Data

(60) Provisional application No. 60/881,905, filed on Jan. 22, 2007.

(51) Int. Cl.
*A61M 5/00* (2006.01)
(52) U.S. Cl.
USPC ............................................. 604/173
(58) Field of Classification Search
CPC .......... A61M 5/3298; A61M 37/0015; A61M 2037/0023; A61M 2037/003; A61M 2037/0038; A61M 2037/0046; A61K 9/0021
USPC ............... 604/22, 46, 47, 115, 117, 173, 180, 604/264, 272, 298, 304, 307, 890.1, 305, 604/306
See application file for complete search history.

(56) References Cited

U.S. PATENT DOCUMENTS

| | | | |
|---|---|---|---|
| 1,554,510 | A | 9/1925 | Kirby |
| 1,770,632 | A | 7/1930 | Smith |
| 2,046,240 | A | 6/1936 | Bayley |
| 2,434,407 | A | 1/1948 | George |
| 3,675,766 | A | 7/1972 | Rosenthal |
| 3,704,194 | A | 11/1972 | Harrier |
| 3,814,097 | A | 6/1974 | Ganderton et al. |

(Continued)

FOREIGN PATENT DOCUMENTS

| | | |
|---|---|---|
| CA | 2376285 | 12/2000 |
| CA | 2316534 | 3/2001 |

(Continued)

OTHER PUBLICATIONS

Rydberg et al. "Low-Molecular-Weight Heparin in Preventing and Treating DVT". Am Fam Physician. Mar. 15, 1999; 59(6):1607-12.*

(Continued)

*Primary Examiner* — Kami A Bosworth
(74) *Attorney, Agent, or Firm* — Jacqueline F. Mahoney; Judy M. Mohr; McDermott Will & Emery LLP

(57) ABSTRACT

A microneedle applicator is provided which has two roughly concentric portions which may be, for example, a solid disk and an annulus surrounding it. On the skin-facing side of the inner portion of the applicator a microneedle array is located. The outer portion of the applicator is placed against the skin, contacting it at a zone. The microneedle array is then pressed towards the skin.

28 Claims, 20 Drawing Sheets

(56) References Cited

U.S. PATENT DOCUMENTS

| | | |
|---|---|---|
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,966,159 A | 10/1990 | Maganias |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,190,558 A | 3/1993 | Ito |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabenau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,873,849 A | 2/1999 | Bernard |
| 5,879,326 A | 3/1999 | Godshall et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,256,533 B1 | 7/2001 | Yuzhakov et al. |
| 6,312,612 B1 | 11/2001 | Sherman et al. |
| 6,322,808 B1 * | 11/2001 | Trautman et al. ............. 424/448 |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kliener et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Rijswijck et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,516,223 B2 | 2/2003 | Hofmann |
| 6,532,386 B2 | 3/2003 | Sun et al. |

(56) References Cited

U.S. PATENT DOCUMENTS

| | | |
|---|---|---|
| 6,533,884 B1 | 3/2003 | Mallik |
| 6,537,242 B1 * | 3/2003 | Palmer ........................ 604/22 |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 * | 6/2004 | Prausnitz et al. ........... 604/239 |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 7,011,844 B2 | 3/2006 | Gale et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,572,405 B2 | 8/2009 | Sherman et al. |
| 7,578,954 B2 | 8/2009 | Gartstein et al. |
| 7,611,481 B2 | 11/2009 | Cleary et al. |
| 7,763,203 B2 | 7/2010 | Arias et al. |
| 2001/0023324 A1 | 9/2001 | Pronovost et al. |
| 2002/0006355 A1 | 1/2002 | Whiston |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0193729 A1 | 12/2002 | Cormier et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 * | 11/2003 | Lastovich et al. ............... 604/47 |
| 2003/0220656 A1 | 11/2003 | Gartstein et al. |
| 2004/0087992 A1 | 5/2004 | Gartstein et al. |
| 2004/0096455 A1 | 5/2004 | Maa et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho et al. |
| 2004/0204669 A1 | 10/2004 | Hofmann |
| 2004/0220535 A1 | 11/2004 | Canham |
| 2004/0236271 A1 | 11/2004 | Theeuwes et al. |
| 2005/0089554 A1 | 4/2005 | Cormier et al. |
| 2005/0096586 A1 | 5/2005 | Trautman et al. |
| 2005/0163827 A1 | 7/2005 | Zech et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2006/0076718 A1 | 4/2006 | Sherman et al. |
| 2006/0095061 A1 | 5/2006 | Trautman et al. |
| 2006/0129174 A1 | 6/2006 | Gartstein et al. |
| 2007/0027427 A1 | 2/2007 | Trautman et al. |
| 2008/0114298 A1 * | 5/2008 | Cantor et al. .................. 604/117 |
| 2008/0183144 A1 | 7/2008 | Trautman et al. |
| 2008/0195035 A1 * | 8/2008 | Frederickson et al. ......... 604/22 |
| 2008/0269685 A1 | 10/2008 | Singh et al. |
| 2009/0155330 A1 | 6/2009 | Ghartey-Tagoe et al. |
| 2010/0028390 A1 | 2/2010 | Cleary et al. |

FOREIGN PATENT DOCUMENTS

| | | |
|---|---|---|
| CA | 2422907 | 4/2002 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 | 3/2001 |
| EP | 1174078 | 1/2002 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |

(56) References Cited

FOREIGN PATENT DOCUMENTS

| | | |
|---|---|---|
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2006-341089 A | 12/2006 |
| SU | 1641346 | 4/1991 |
| SU | 1667864 | 8/1991 |
| WO | WO 93/15701 | 8/1993 |
| WO | WO 93/17754 | 9/1993 |
| WO | WO 94/23777 | 10/1994 |
| WO | WO 95/22612 | 8/1995 |
| WO | WO 95/33612 | 12/1995 |
| WO | WO 96/00109 | 1/1996 |
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/13544 | 4/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/28307 | 7/1998 |
| WO | WO 99/00155 | 1/1999 |
| WO | WO 99/29298 | 6/1999 |
| WO | WO 99/29364 | 6/1999 |
| WO | WO 99/29365 | 6/1999 |
| WO | WO 99/61888 | 12/1999 |
| WO | WO 99/64580 | 12/1999 |
| WO | WO 00/05166 | 2/2000 |
| WO | WO 00/35530 | 6/2000 |
| WO | WO 00/70406 | 11/2000 |
| WO | WO 00/74763 | 12/2000 |
| WO | WO 00/74764 | 12/2000 |
| WO | WO 00/74765 | 12/2000 |
| WO | WO 00/74766 | 12/2000 |
| WO | WO 00/77571 | 12/2000 |
| WO | WO 01/08242 | 2/2001 |
| WO | WO 01/36037 | 5/2001 |
| WO | WO 01/36321 | 5/2001 |
| WO | WO 01/49362 | 7/2001 |
| WO | WO 02/02180 | 1/2002 |
| WO | WO 02/07543 | 1/2002 |
| WO | WO 02/07813 | 1/2002 |
| WO | WO 02/17985 | 3/2002 |
| WO | WO 02/32331 | 4/2002 |
| WO | WO 02/32480 | 4/2002 |
| WO | WO 02/062202 | 8/2002 |
| WO | WO 02/072189 | 9/2002 |
| WO | WO 02/091922 | 11/2002 |
| WO | WO 02/100474 | 12/2002 |
| WO | WO 03/024290 | 3/2003 |
| WO | WO 03/024518 | 3/2003 |
| WO | WO 2004/076339 | 9/2004 |
| WO | WO 2004/110717 | 12/2004 |
| WO | 2005/089857 A1 | 9/2005 |
| WO | WO 2005/094526 | 10/2005 |
| WO | WO 2006/020842 | 2/2006 |
| WO | WO 2006/055795 | 5/2006 |
| WO | WO 2007/002523 | 1/2007 |
| WO | WO 2007/124411 | 11/2007 |
| WO | 2008/011625 A2 | 1/2008 |
| WO | 2008/091602 A2 | 7/2008 |
| WO | 2008/130587 A2 | 10/2008 |
| WO | 2009/048607 A1 | 4/2009 |

OTHER PUBLICATIONS

"Heparin Pregnancy and Breast Feeding Warnings". Drugs.com. Accessed Oct. 8, 2009. <http://www.drugs.com/pregnancy/heparin.html>.*

"extend". Merriam-Webster Online Dictionary. <http://www.merriam-webster.com/dictionary/extend>.*

"extend". Macmillan Online Dictionary. <http://www.macmillandictionary.com/dictionary/american/extend>.*

PCT Search Report dated Jul. 18, 2008.

Chun, et al., "An array of hollow microcapillaries for the controlled injection of genetic materials into animal/plant cells," IEEE Workshop on Micro Electro Mechanical Systems, pp. 406-411, (1999).

Henry, et al., "Micromachined microneedles for transdermal delivery of drugs", IEEE Workshop on Micro Electro Mechanical Systems, New York, NY, pp. 494-498, (1998).

Henry, et al., "Microfabricated microneedles: A novel approach to transdermal drug delivery", J. Pharmaceutical Science, vol. 87, No. 8, pp. 922-925, (1998).

International Search Report from PCT/US2000/015612 mailed on Sep. 7, 2000.

International Search Report from PCT/US2000/015613 mailed on Sep. 6, 2000.

International Search Report from PCT/US2000/015614 mailed on Sep. 6, 2000.

International Search Report from PCT/US2001/031977 mailed on Apr. 29, 2002.

International Search Report from PCT/US2001/031978 mailed on Apr. 29, 2002.

International Search Report from PCT/US2002/014624 mailed on Sep. 3, 2002.

International Search Report from PCT/US2002/029228 mailed on Apr. 23, 2003.

International Search Report from PCT/US2002/029245 mailed on Dec. 27, 2002.

International Search Report from PCT/US2004/005382 mailed on Nov. 25, 2004.

International Search Report from PCT/US2004/017255 mailed on May 24, 2005.

International Search Report from PCT/US2005/009854 mailed on Jul. 3, 2008.

Matriano, et al., "Macroflux(R) microprojection array patch technology: A new and efficient approach for intracutaneous immunization", Pharm. Res., vol. 19, No. 1, pp. 63-70, (2002).

McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.

Mikszta, et al., "Improvred genetic immunization via micromechanical disruption of skin-barrier function and targeted epidermal delivery", Nat. Med., vol. 8, No. 4, pp. 415-419, (2002).

Mikszta, et al., "Protective immunization against inhalation anthrax: A comparison of minimally invasive delivery platforms", J. Inf. Dis., vol. 191, No. 2, pp. 278-288, (2005).

Papautsky, et al., "Micromachined Pipette Arrays," MPA, Proceedings-19th international Conference-IEEE/EMBS, Chicago IL, USA, pp. 2281-2284 (1997).

Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).

Prausnitz, et al., "Transdermal transport efficiency during skin electroporation and iontophoresis", J. Contr. Release, vol. 38, pp. 205-217, (1996).

Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).

(56) References Cited

OTHER PUBLICATIONS

Sivamani, et al., "Microneedles and transdermal applications", Exp. Opin. Drug Del., vol. 4, No. 1, pp. 19-25, (2007).

Wouters, et al., "Microelectrochemical systems for drug delivery", Electrochimica Acta., vol. 42, pp. 3385-3390, (1997).

Xia, et al., "Soft Lithography", Angew. Chem. Int. Ed., vol. 37, pp. 551-575, (1998).

Xia, et al., "Soft Lithography", Annu. Rev. Mater. Sci., vol. 28, pp. 153-184 (1998).

"Heparin Pregnancy and Breast Feeding Warnings", Drugs.com, Accessed Oct. 8, 2009, <http://www.drugs.com/pregnancy/heparin.html>.

International Search Report from PCT/US2008/004943 mailed on Jun. 9, 2009, application published as WO 2008/130587 on Oct. 30, 2008.

International Search report from PCT/US2008/011635 mailed on Dec. 19, 2008, application published as WO 2009/048607 on Apr. 16, 2009.

Rydberg, et al., "Low-molecular-weight heparin preventing and treating DVT", Am. Fam. Physican, vol. 59, No. 6, pp. 1607-1612, (1999).

* cited by examiner

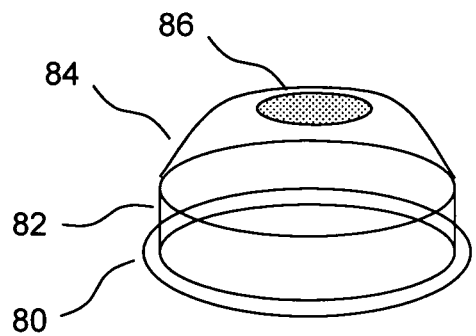
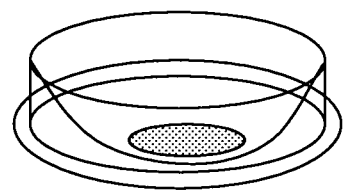
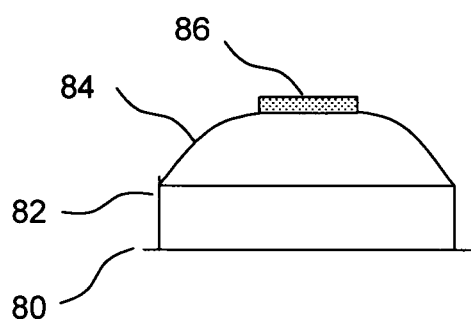
FIG. 7A
FIG. 7B
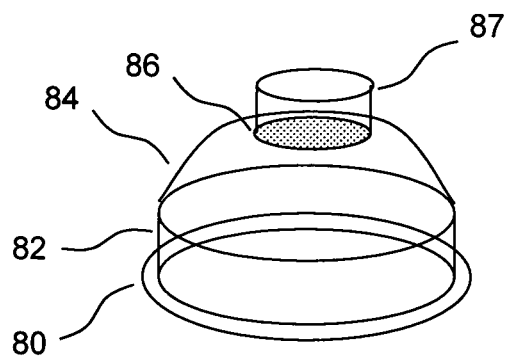
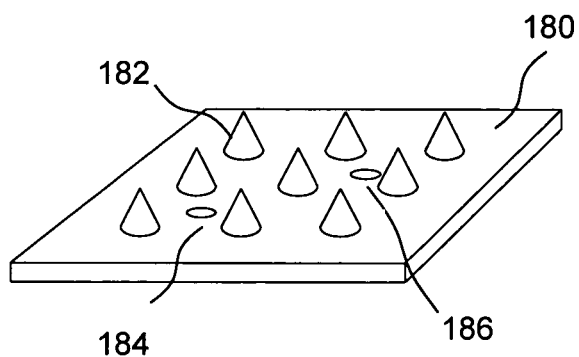
FIG. 7C
FIG. 7D

APPLICATORS FOR MICRONEEDLES

CROSS-REFERENCE TO RELATED APPLICATIONS

This application claims priority to U.S. Provisional Patent Application No. 60/881,905, filed Jan. 22, 2007, which is incorporated by reference herein.

TECHNICAL FIELD

This invention relates generally to drug delivery and diagnostics performed with the assistance of microneedles or similar systems of microprojections or microprotrusions.

BACKGROUND

Arrays of microneedles were proposed as a way of administering drugs through the skin in the 1970s, for example in expired U.S. Pat. No. 3,964,482. Microneedle arrays can facilitate the passage of drugs through human skin and other biological membranes in circumstances where ordinary transdermal administration is inadequate. Microneedle arrays can also be used to sample fluids found in the vicinity of a biological membrane such as interstitial fluid, which is then tested for the presence of biomarkers.

In recent years it has become more feasible to manufacture microneedle arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use.

In addition to cost, integrity, and sterility, a further issue with microneedle arrays is bioavailability of the active agent. An intravenous injection delivers a precise quantity of an active agent to the circulation. A subcutaneous or intramuscular injection delivers a precise quantity of an active agent into the tissue, but the quantity of active agent delivered to the circulation and the rate at which active ingredient is delivered are affected by the type of surrounding tissue, circulation, and possibly other factors. When a drug is delivered orally, the resulting blood levels may exhibit substantial variation among patients due to metabolism and other factors, but minimal therapeutic levels can be assured for most patients, for example, because the speed of metabolism has an upper limit and because there is long experience with the absorption of many drugs from oral formulations. When a drug is delivered to unmodified skin by a conventional transdermal patch, the bypassing of the hepatic circulation may lessen the effect of liver metabolism on bioavailability. On the other hand, with a conventional transdermal patch, differences in skin permeability are an additional factor leading to differences in bioavailability.

Microneedles manipulate the permeability of the skin with respect to the active agent. Variability in the permeability enhancement created by different applications of the microneedles will result in variations in the rate of transfer through the skin, the amount transferred through the skin and the bioavailability. Variability of skin permeability enhancement on the application of a microneedle array can result from application on different patients. Particular concern exists, of course, if the enhancement is small in particular patient populations so that the administration of the drug will not produce a therapeutically effective dosing (e.g., adequate blood levels) in those populations. Concern may arise also if the enhancement is sometimes undesirably small in a patient, even if at other times the enhancement is as expected in that patient, depending on details of how and where the microneedle array is applied.

A typical microneedle array comprises microneedles projecting from a base of a particular thickness, which may be of any shape, for example square, rectangular, triangular, or circular. The microneedles themselves may have a variety of shapes. While an array could be pressed by hand into skin, it has also been proposed to use a variety of devices to hold the microneedle array as it is being applied or to facilitate in one way or another the process of microneedle array application to the skin or other biological membrane. Such devices may broadly be referred to as "applicators." Applicators may for example reduce the variations in force, velocity, and skin tension that occur when a microneedle array is pressed by hand into the skin. Variations in force, velocity and skin tension can result in variations in permeability enhancement.

In some applications of microneedle arrays, they may be applied to the skin or other biological membrane in order to form microchannels and then more or less immediately withdrawn. In other applications the microneedle array may be held in place for a longer period of time. The design of the applicator may naturally be influenced by how long the microneedles are expected to stay in place.

In the use of microneedle arrays, particularly when the arrays are kept in place for a prolonged period of time, devices to transport the drug substance to the skin may be employed. A very simple such device may, for example, comprise a reservoir for liquid or solid drug substance which is kept in contact with the base, with the liquid drug substance flowing through small apertures in the base or by diffusion when solid drug substance is used. Another device suitable for delivering the drug substance to skin is described in U.S. Published Patent Application No. 2005/0094526. Rotary applicators have been disclosed in U.S. Published Patent Application No. 2004/0087992. There is some disclosure relating to applicators, for example, in U.S. Pat. Nos. 6,537,242, 6,743,211 and 7,087,035.

There is therefore a need in the art for applicators and related devices suitable for use with microneedle arrays, for example, in order to assist in making the process of drug delivery more user friendly and uniform across patients and for different applications to the same patient.

SUMMARY OF THE INVENTION

In one aspect of the invention, a microneedle applicator is provided which has two roughly concentric portions which may be, for example, a solid disk and an annulus surrounding it. On the skin-facing side of the inner portion of the applicator a microneedle array is located. The outer portion of the applicator is placed against the skin, contacting it at a zone. The microneedle array is then pressed towards the skin.

In another aspect of the invention, an applicator for a microprojection array is provided which comprises an inner and an outer portion. The microprojection array attaches to or is integral with the inner portion. The outer portion comprises a contact zone for contacting skin, and the shape of the applicator may be varied between a first and second stable configurations. The inner and outer portions may be integral with each other. The variation in the shape of the applicator may be used to press microprojections into the skin.

In another aspect of the present invention, an expanding microneedle array is provided which comprises elongated members at an angle to the microneedles. The members or the attachments between them are sufficiently flexible to allow the microneedles some limited degree of motion which is perpendicular to the needles. The ends of the members which in use will be further from the skin are so arranged that they may be pressed towards the skin with the resulting pressure being transmitted to the microneedles, resulting in the microneedles being moved apart as they are pressed into the skin.

In another aspect of the present invention, a laminate bonds to the surface of the skin which is to be penetrated with projections. The laminate is stiffer than the skin and thinner than the length of the projections. The laminate may be perforated to permit the projections to pass through the holes in the film. The laminate may be continuous and the projections would penetrate it and the skin. The laminate may be a polymer film or a woven or non-woven fabric with an adhesive to attach it to the skin. The laminate may be a liquid that is applied to the skin and forms a film. The laminate normalizes the extensibility of the skin for all patients reducing the effect of patient-to-patient variability on penetration of the skin with the projections.

FIGURES

FIG. 1A schematically depicts a shape-changing microneedle applicator of the invention as seen from below (i.e., looking at the portion of the application from which the microneedles project). FIG. 1B schematically depicts the same applicator in perspective from below with adhesive attached. FIG. 1C depicts the same applicator in a somewhat different perspective view without adhesive attached.

FIG. 2 schematically depicts a similar shape-changing microneedle applicator in cross section.

FIG. 3A depicts a different shape-changing microneedle applicator of the invention as seen from above. FIG. 3B depicts the same applicator in a side view. FIG. 3C depicts the same applicator as seen looking directly down on it and in cross-sectional view.

FIG. 4 schematically depicts the shapes assumed by the applicators of FIGS. 1A-1C and FIG. 2 when one of them is placed in use.

FIG. 5 schematically depicts an alternate set of shapes which an applicator having the overall shape of FIGS. 1A-1C or FIG. 2 could assume when placed in use.

FIG. 6 schematically depicts another set of shapes which an applicator having the overall shape of FIGS. 1A-1C or FIG. 2 could assume when placed in use.

FIGS. 7A-7B schematically depict an alternative shape-changing microneedle applicator of the invention. FIG. 7C schematically depicts an application like that of FIGS. 7A-7B with an additional reservoir for fluid to be applied. FIG. 7D is a schematic enlarged view of part of the microneedle array, showing channels through which fluid may pass.

FIG. 8 depicts an approximate force-displacement curve for shape-changing applicators such as those in FIGS. 1A-1C and 2.

FIG. 9 schematically depicts an expanding microneedle array with elongated members at an angle to the microneedles.

FIG. 10 schematically depicts an alternative embodiment of an expanding microneedle array with elongated members at an angle to the microneedles.

FIG. 11 schematically depicts the operation of a class of devices suitable for tensioning skin as a microneedle array is pressed down on the skin.

Figure 15:
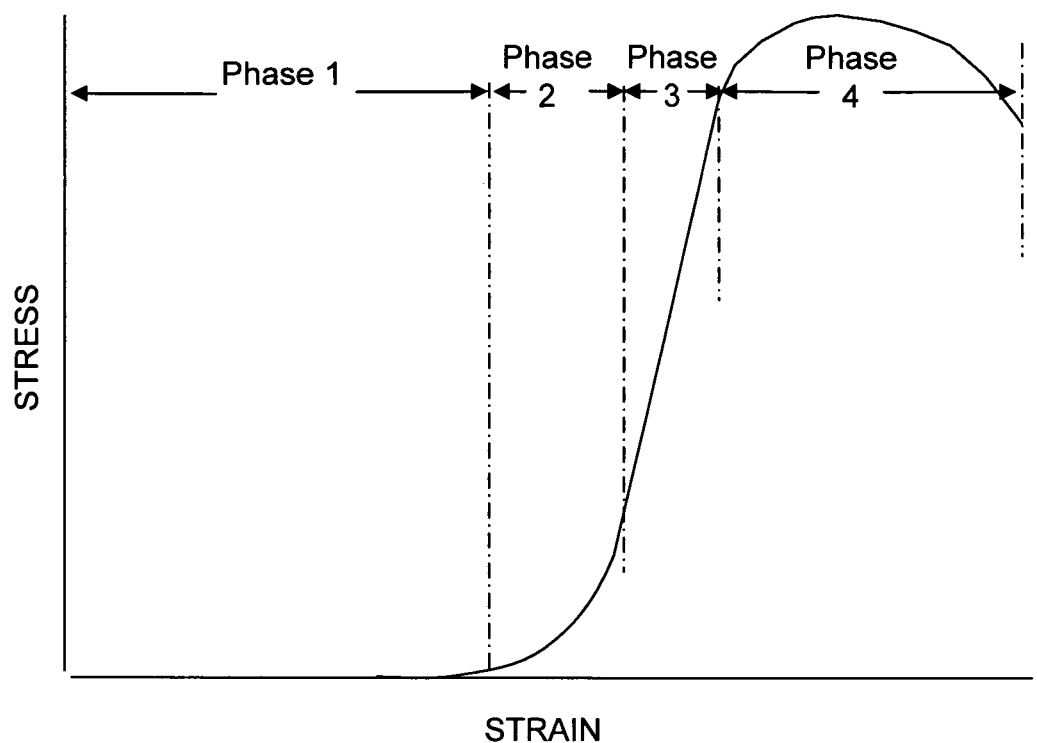

FIG. 15 (prior art) schematically depicts a general form of the human skin strain-stress curve.

Figure 1A:
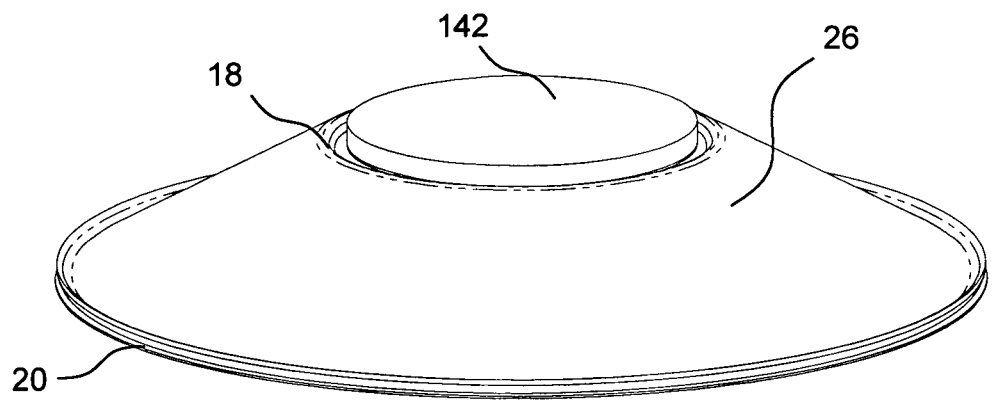
Figure 1B:
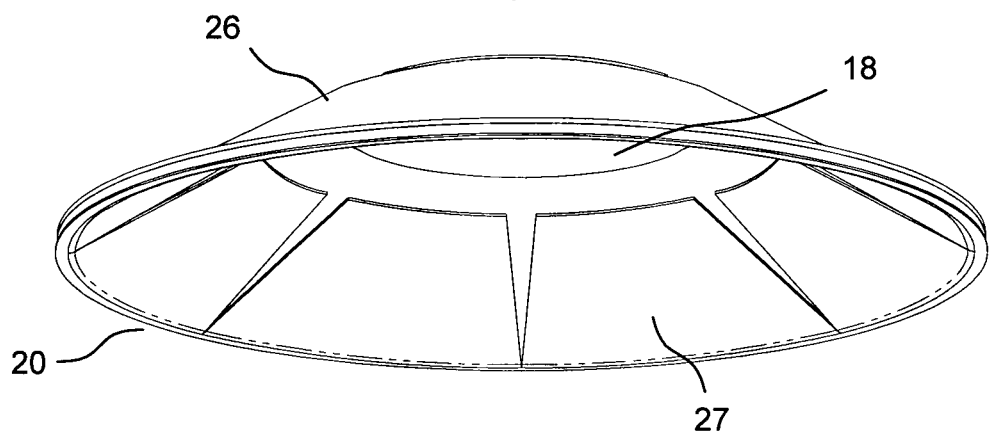
Figure 16A:
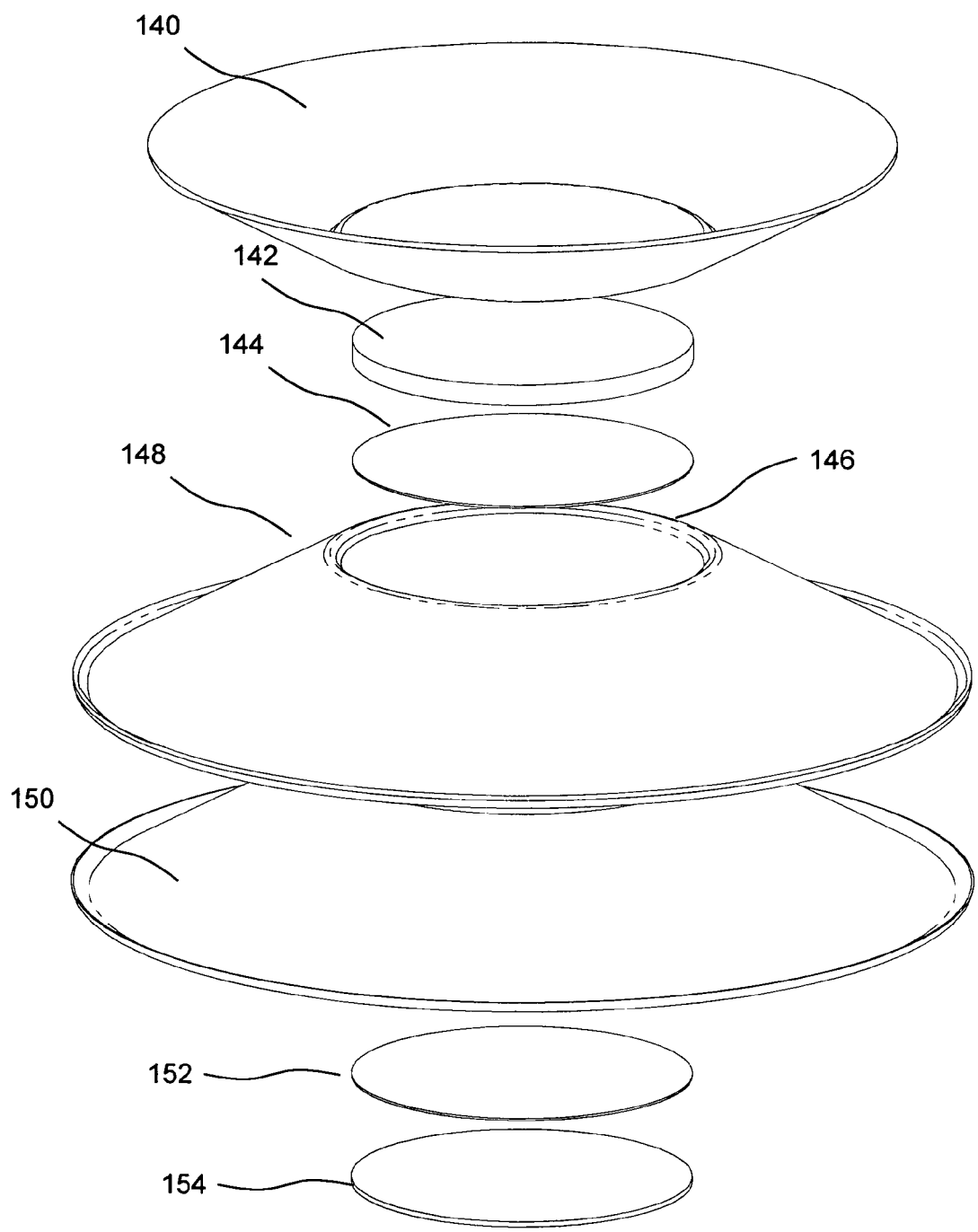
Figure 16B:
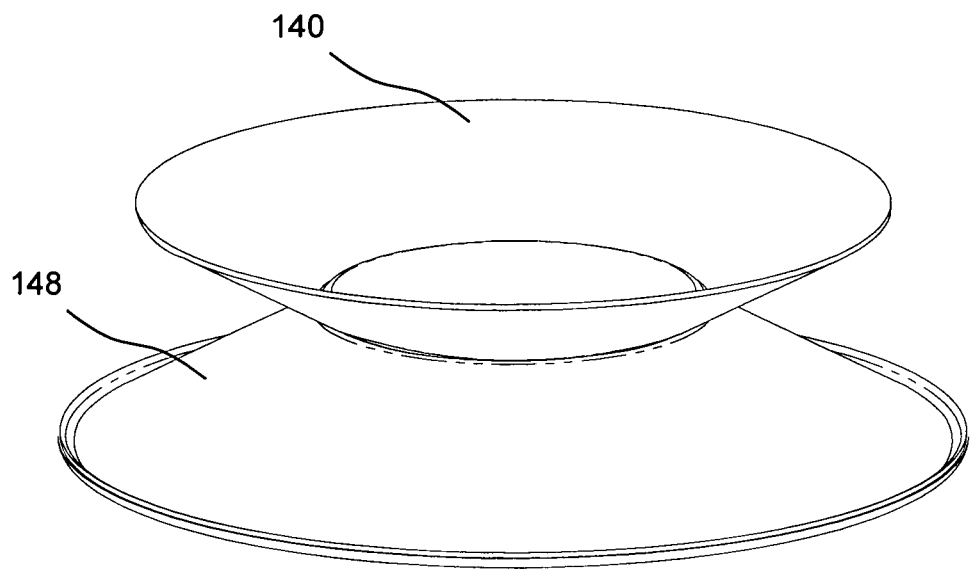

FIG. 16A schematically depicts in an exploded view an applicator similar to that of FIGS. 1A-1B with an added component. FIG. 16B schematically depicts the same applicator, not exploded, in perspective.

Figure 17A:
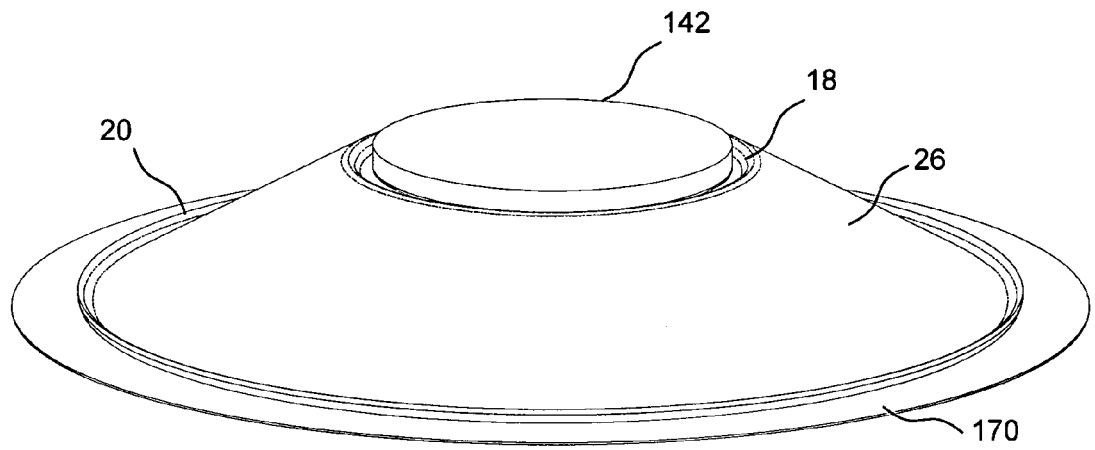
Figure 17B:
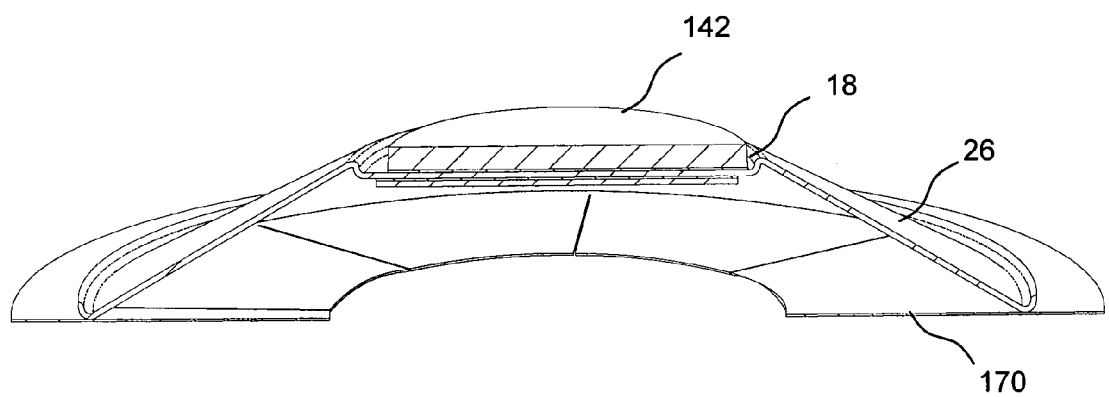

FIGS. 17A-17B schematically depict an applicator of the invention, similar to that of FIGS. 1A-1B, with skin adhesive attached. FIG. 17A is a perspective view from above, whereas FIG. 17B is a cross-sectional view.

Figure 18:
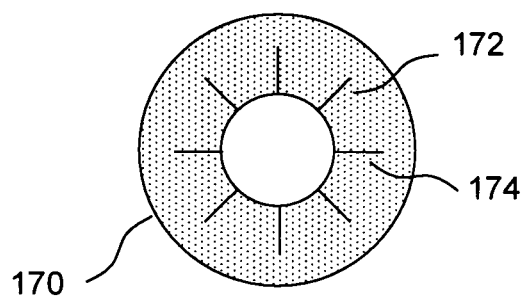

FIG. 18 schematically depicts a possible form of adhesive for application to skin in connection with certain applicators of the invention.

Figure 19A:
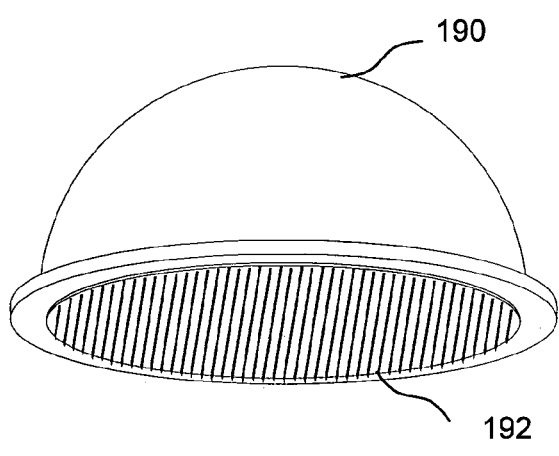
Figure 19B:
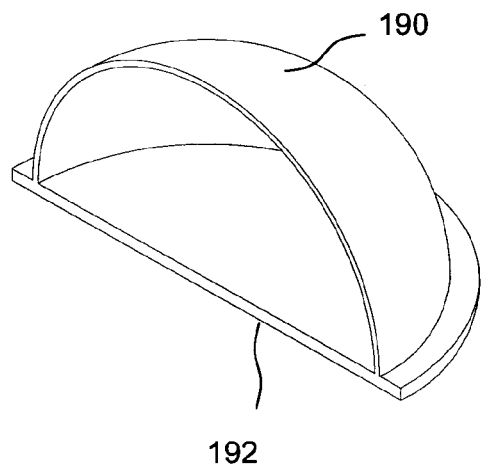

FIG. 19A-19B schematically depict a further embodiment of an applicator of the invention.

DESCRIPTION OF PREFERRED EMBODIMENTS

Before describing the present invention in detail, it is to be understood that this invention is not limited to specific materials or device structures or geometries, as such may vary. It is also to be understood that the terminology used herein is for the purpose of describing particular embodiments only, and is not intended to be limiting.

As used in this specification and the appended claims, the singular forms "a," "an," and "the" include both singular and plural referents unless the context clearly dictates otherwise. Thus, for example, reference to "an active ingredient" includes a plurality of active ingredients as well as a single active ingredient, reference to "a temperature" includes a plurality of temperatures as well as single temperature, and the like.

In this application reference is often made for convenience to "skin" as the biological membrane which the microneedles penetrate. It will be understood by persons of skill in the art that in most or all instances the same inventive principles apply to the use of microneedles to penetrate other biological membranes such as, for example, those which line the interior of the mouth or biological membranes which are exposed during surgery.

In this application reference is also made to "microneedles" as the type of microprotrusion or microprojection which is being employed. It will be understood by persons of skill in the art that in many cases the same inventive principles apply to the use of other microprotrusions or microprojections to penetrate skin or other biological membranes. Other microprotrusions or microprojections may include, for example, microblades as described in U.S. Pat. No. 6,219,574 and Canadian patent application no. 2,226,718, and edged microneedles as described in U.S. Pat. No. 6,652,478.

In discussing the applicators of this invention, the term "downward" is sometimes used to describe the direction in which microprotrusions are pressed into skin, and "upward" to describe the opposite direction. However, those of skill in the art will understand that the applicators can be used where the microprotrusions are pressed into skin at an angle to the direction of the earth's gravity, or even in a direction contrary to that of the earth's gravity.

The sizes of the microneedles and other protrusions for use with this invention will be a function of the manufacturing technology and of the precise application. In general, however, microneedles and other microprotrusions used in practice may be expected to have a length of about 20 to about 1000 microns, more preferably from about 50 to about 750 microns and most preferably from about 100 to about 500 microns. Often it will be desired that the microprotrusions will be long enough to penetrate through the stratum corneum layer of skin at some suitable point of application on the human body, for example the thigh, hip, arm, or torso.

The term "microneedle array" for purposes of this invention is intended to denote a two-dimensional or three-dimensional arrangement of microneedles. The arrangement may be regular according to a repeating geometric pattern or it may be irregular. Similarly, "microprojection array" denotes a two-dimensional or three-dimensional arrangement of microprojections.

In one aspect of the invention, a microneedle applicator is provided which has two roughly concentric portions which may be, for example, a solid disk and an annulus surrounding it. On the skin-facing side of the inner portion of the applicator a microneedle array is located. The outer portion of the applicator is placed against the skin, contacting it at a zone. The microneedle array is then pressed towards the skin.

In a particular variant on the preceding, the outer member moves upward. The zone where the outer member contacts the skin may have an adhesive or abrasive so that movement of the outer member away from the skin pulls on the skin.

In an alternative variant on the preceding, the microneedle array may be pressed sufficiently far down that it lies below the position of the outer member. The outer member may again be provided with an adhesive or abrasive which contacts the skin.

Figure 1C:
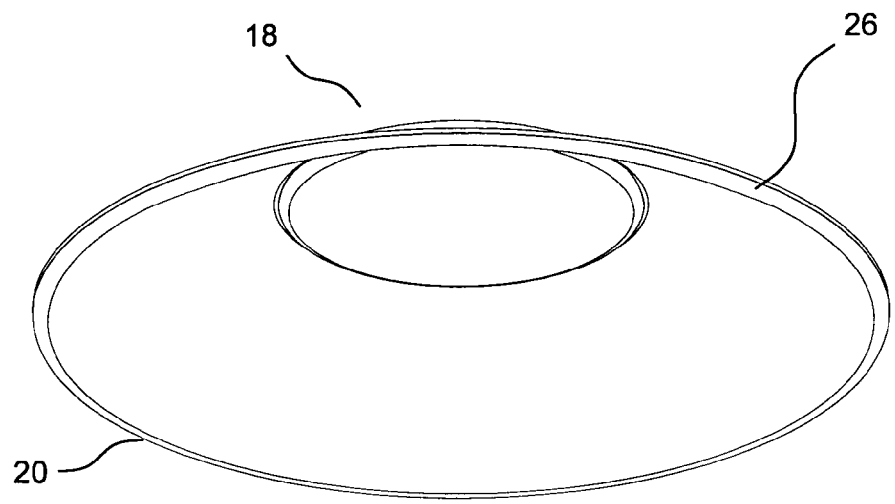

FIGS. 1A-1C illustrate an exemplary applicator corresponding to the concentric concept described above. FIG. 1A depicts the applicator as seen from above. There is a central or inner portion 18 and concentric to it an outer portion 26. The outer portion contacts the skin initially at a contact zone 20. Atop the inner portion 18 there is a "button" 142, attached to the inner portion, for example, with an adhesive. The button may be stiffer than the inner and outer portions of the applicator, for example, by virtue of being thicker. FIG. 1B depicts the applicator as seen from below, i.e., from the side which is close to skin. The microneedle array is attached to the underside of the central portion 18. In addition, adhesive 27 may be attached to part of the underside of the central portion 18. The central and outer portions are preferably made integrally with each other.

FIG. 1C schematically depicts the applicator of FIG. 1A-1B, without adhesive 27 and in a somewhat different perspective view. The applicator's outer portion 26 has roughly the shape of a truncated cone (frustum of a cone).

Figure 2:
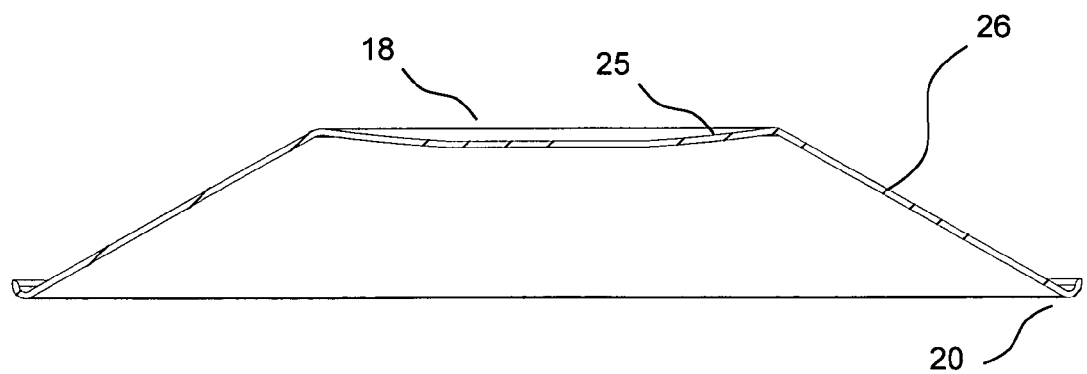

FIG. 2 schematically depicts a quite similar applicator in cross-section. The applicator's inner member 18 as depicted in FIG. 2 has a shape which projects modestly towards the skin. The shape has (in comparison with the applicator of FIGS. 1A-1C) a more gradually sloping indentation 25 in the center. This kind of gradually sloping indentation is useful to allow a slight variability in the pressure exerted on the skin by a microprojection array affixed to the inner member.

Figure 3A:
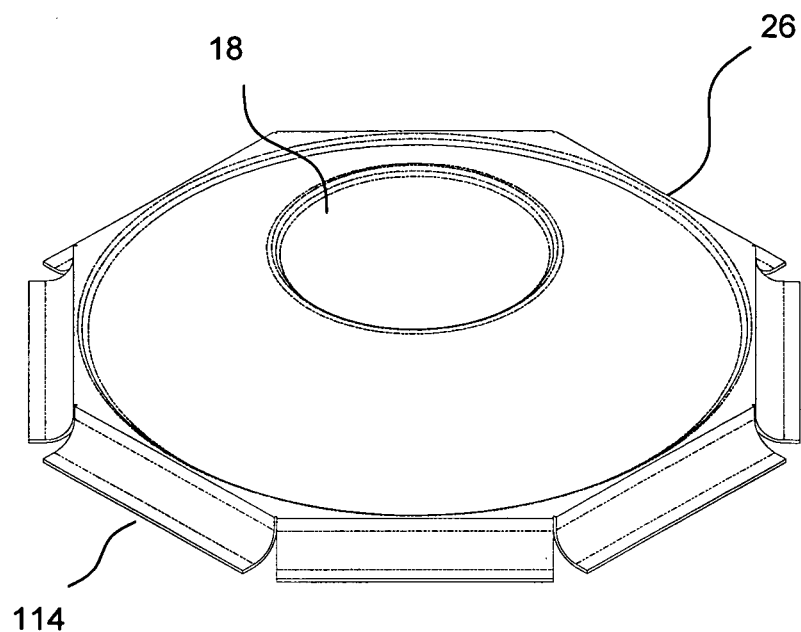
Figure 3B:
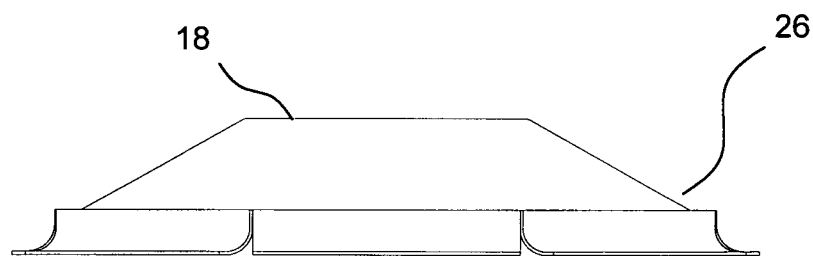
Figure 3C:
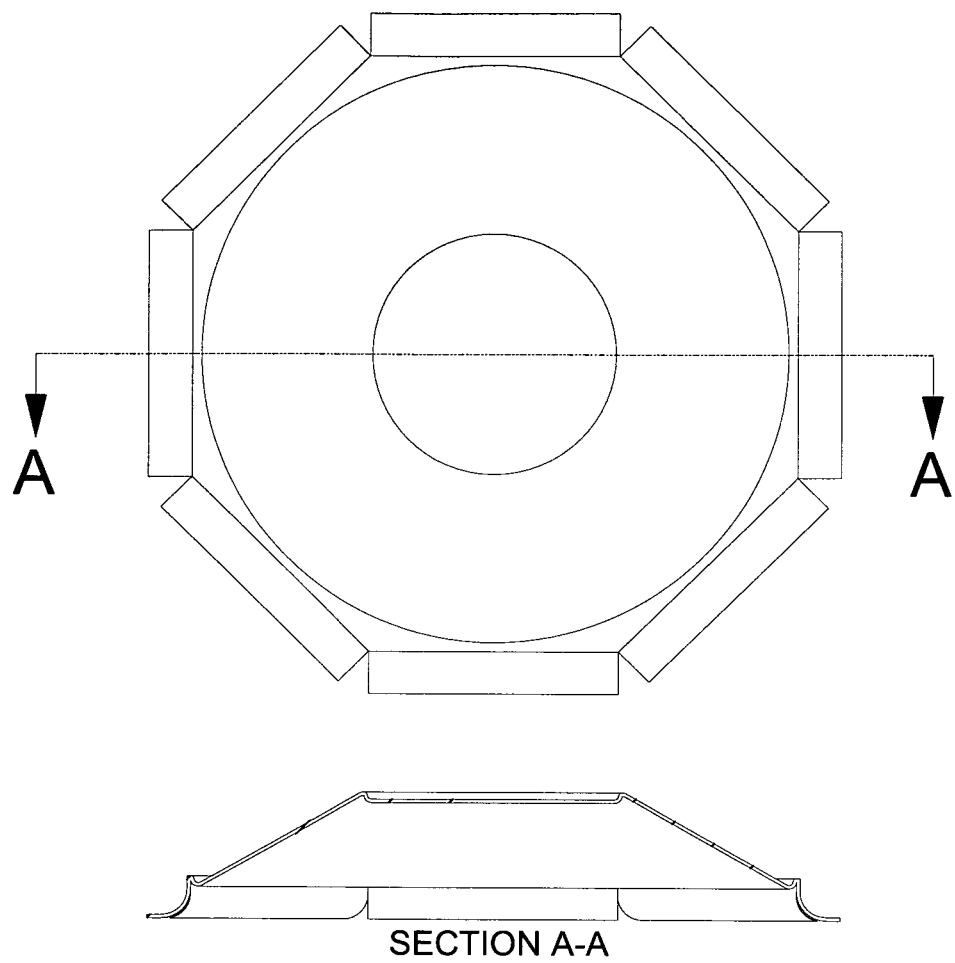

FIG. 3A depicts a different shape-changing microneedle applicator of the invention as seen from above. FIG. 3B depicts the same applicator in a side view. FIG. 3C depicts the same applicator as seen looking directly down on it and in cross-sectional view. It may be seen that the applicator of FIGS. 3A-3C has a shape similar to that of FIGS. 1A-1C except for the presence of eight outwardly pointing members around the edge of the device (for example 114) which each have approximately the shape of a quarter cylinder.

Figure 4:
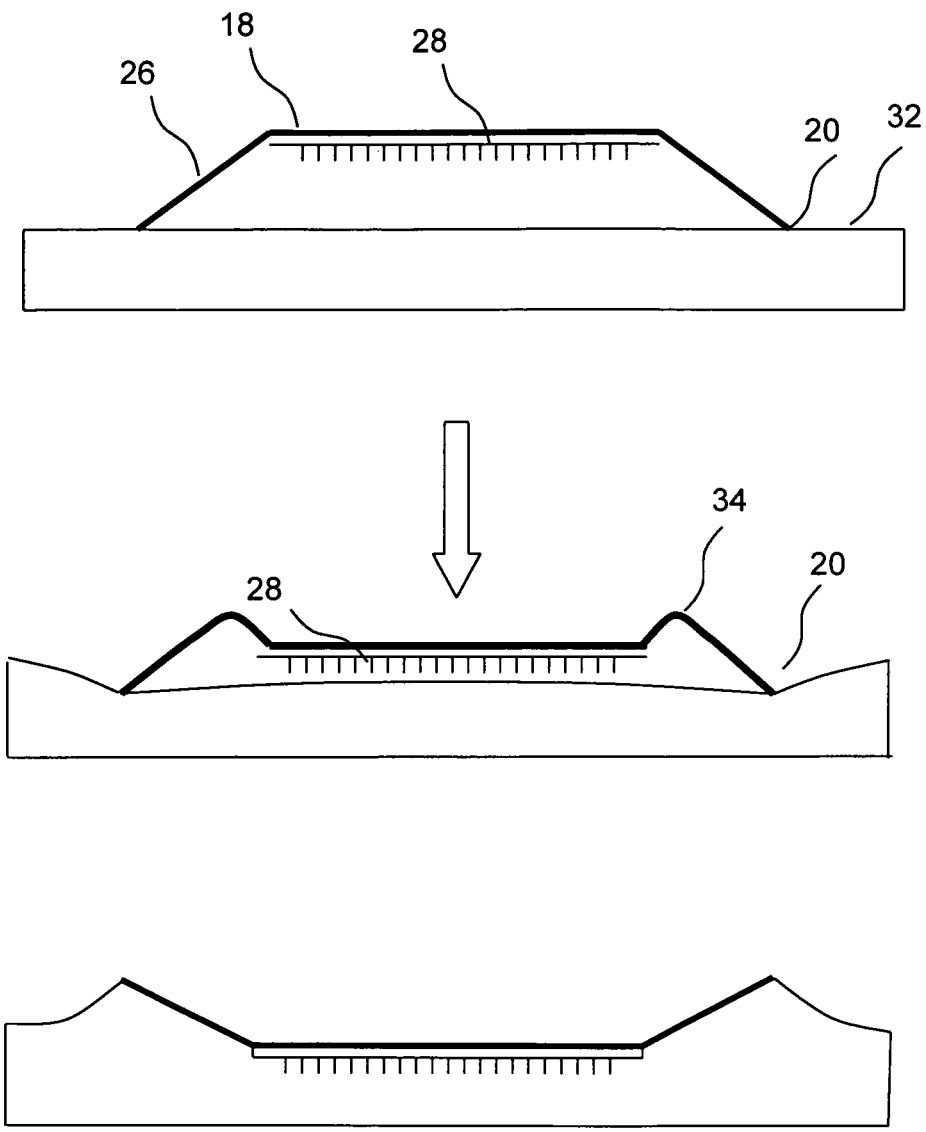

FIG. 4 schematically depicts the deformation undergone by the applicators of FIGS. 1A-1C or 2 as they are placed in use. The different panels of FIG. 4 all show the applicator and the skin 32 to which it is applied in cross section. As may be seen, when pressure is applied above the microneedle array 28, the applicator deforms elastically. At a particular point in the deformation, a bend 34 forms. The deformation continues until, as the microneedles approach the skin, the relationship between the inner portion of the applicator and the outer member inverts, with the latter extending at an angle away from, rather than towards, the skin. The shape change of the applicator may cause a tensioning of the skin to the extent that the skin moves with it when there is a change of shape. The deformed applicator may be stable in the inverted configuration, so that it remains in that configuration until further force is applied.

Figure 5:
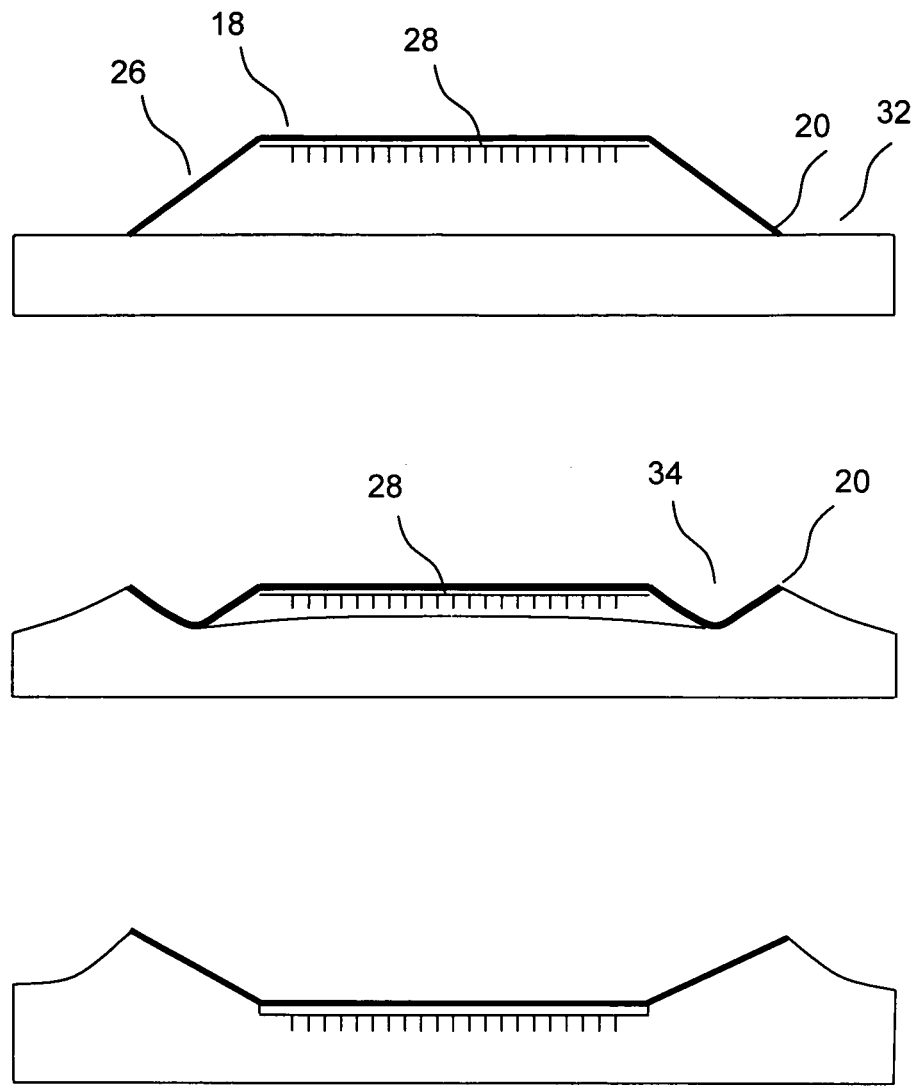

FIG. 5 schematically depicts an alternate set of shapes which an applicator having the overall shape of FIGS. 1A-1C or FIG. 2 could assume when placed in use. A difference between FIG. 5 and FIG. 4 is that the bend 34 has a different directionality. This causes an outer portion of the applicator to remain in contact with the skin in the latter part of the process of deformation.

Figure 6:
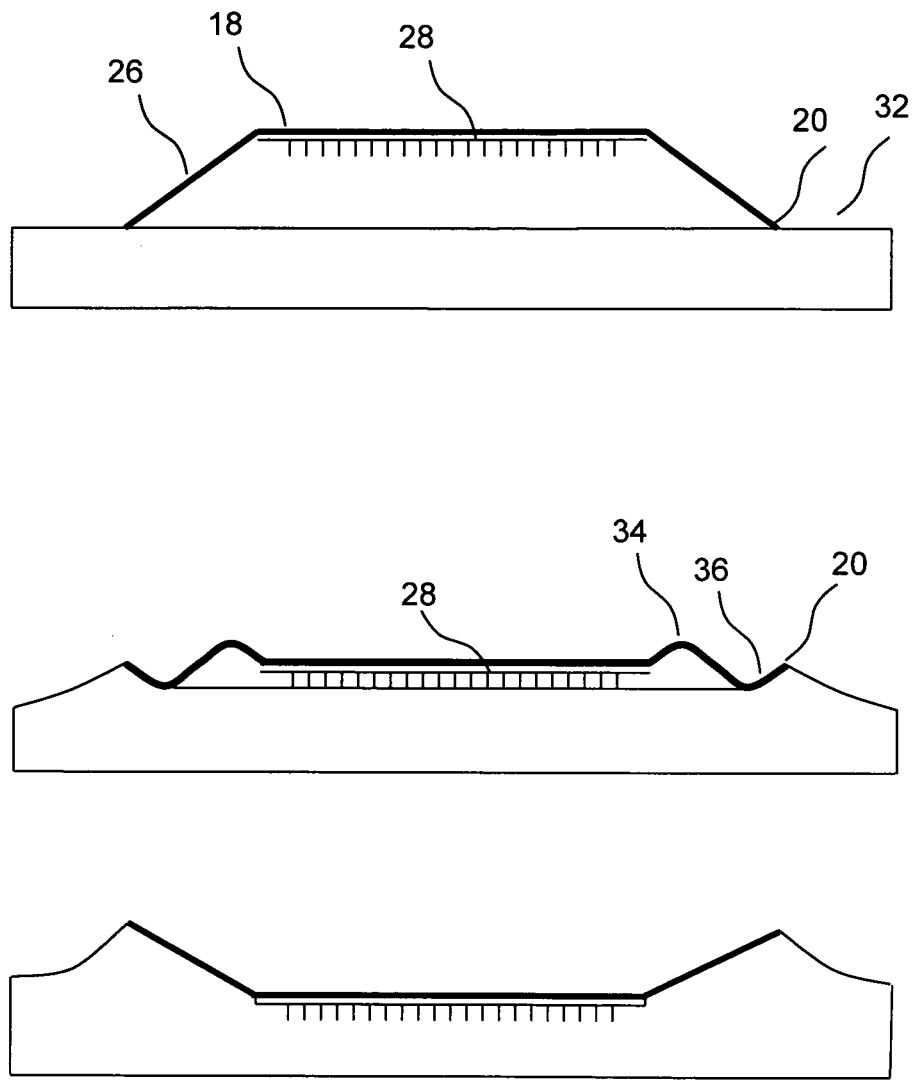

FIG. 6 schematically depicts another set of shapes which an applicator having the overall shape of FIGS. 1A-1C or FIG. 2 could assume when placed in use. A difference between FIG. 6 and FIGS. 4 and 5 is that there are two separate bends 34 and 36 in the applicator as depicted in FIG. 6. With two or more bends, an outer portion of the applicator remains in contact with the skin in the latter part of the process of deformation.

The results of FIGS. 4-6 would generally be expected to require an adhesive applied to some portion of the underside of the outer member. A variety of such adhesives may be employed. For example, a simple two-sided tape, such 3M 1513 which contains acrylate with a PET (polyethylene terephthalate) carrier, may be used if cut to an appropriate shape to largely cover a radially outward section of the underside of the outer member, as shown schematically in FIG. 17A. In that figure, an inner member 18 and outer member 26 are depicted, as well as a button 142, much as in FIG. 1A. In addition, adhesive 170 is shown underneath the applicator, touching the skin contacting zone 20. In FIG. 17B, a perspective view of the same applicator from below, it is seen that the adhesive 170 is sectioned as in FIG. 18.

As an alternative to the placement of adhesive on the outer member of the applicator, it is possible to place adhesive on the skin in a portion of the area where the applicator is expected to make contact with the skin as it is put into use and changes shape as schematically depicted in exemplary FIGS. 4-6. The adhesive for example may have an annular shape 170 with optional radial cuts such as 172 and 174, as shown in FIG. 18. The applicator would be placed in such a way that the microneedle array approaches the skin through the opening of the annular-shaped adhesive 170.

In an alternative embodiment, the microneedle array may not be attached to the applicator of FIGS. 1A-1C and 2. Instead, the array may be placed on the skin, and the applicator then placed over the array and caused to invert.

The outer member of the applicator of FIGS. 1A-1C and 2 may have a variety of shapes. FIG. 2 depicts the outer member as having an approximately straight cross section. The cross-section may however alternatively be convex or concave.

FIG. 16A schematically depicts in an exploded view an applicator related to that of FIGS. 1A-1C and 2, which is provided with an additional structure. In FIG. 16A we see a microneedle array 154 (needles are on the lower side which is not visible in the figure). That array is attached via adhesive 152 to the central disk 146 of the shell 148. Below the shell 148 is a skin adhesive 150 which is attached to the underside of the shell. Over the central disc 146, there is a further adhesive 144 which is used to attach a button or spacer 142, above which the guide 140 is placed.

A purpose of the guide 140 is to distribute evenly the pressure used to invert the configuration of the shell 148 as it is applied to human skin or another biological membrane, compared to applying pressure directly to the button 142. This more even distribution of the load is believed to reduce the possibility of the shell 148 buckling asymmetrically. In the embodiment of FIG. 16A, the guide 140 has a form similar to that of the shell 148, but is inverted and somewhat smaller. FIG. 16B is a non-exploded schematic view of the applicator of FIG. 16A. The guide 140 may also permit the applicator to be grasped in different ways which are more convenient for the person applying the microprojection array to skin, for example with thumb and forefinger around its edge.

A further purpose of the guide 140 may be to limit the upward motion of the shell 148 as the applicator inverts configuration. When the guide is designed so that this is achieved, the applicator's outer portion will contact the guide as the applicator inverts. The guide 140 under those circumstances serves to define in part the second stable configuration of the applicator.

FIGS. 7A-7B schematically depict a different realization of the concentric concept described above. FIG. 7A depicts the applicator prior to use whereas FIG. 7B depicts the applicator in use. In FIG. 7A, the upper panel is a perspective view of the applicator whereas the lower panel is a cross section. As may be seen in FIG. 7A, the applicator comprises a base which has the shape of a ring 80. The lower side of the ring may be coated with a suitable adhesive. Attached to or integral with that base is a cylindrical body 82, which is surmounted by a dome 84. In the center of the dome there is a holder 86 for the microneedles, which may also be integral with the remainder of the applicator. The applicator is designed so as to be placed on the skin, to which the adhesive on the ring 80 may adhere. Once the applicator is on the skin, pressure is applied (for example with a finger) to the holder 86, causing the applicator to invert as shown in FIG. 7B. It may be useful during this application to hold the cylindrical member 82 steady to facilitate the inversion. Upon inversion, the holder 86 contacts the skin, causing the microneedles to penetrate it. The applicator may be so designed that in the inverted position, the holder 86 is slightly below the level of the ring 80, as shown schematically (not to scale) in FIG. 7B. With the skin adhered to the ring 80 by adhesive, the tendency of the holder 86 to go slightly below the level of the ring may cause a modest doming of the skin which tensions the skin between the ring and the holder. Such tensioning can facilitate the entry of the microneedles into skin.

Alternatively, the device described above may be used to apply a microneedle array which is not attached to the holder 86. Instead the microneedle array can be positioned on the skin or anywhere along the path of the holder as it travels towards the skin. During the change of configuration the holder may exert force on the microneedle array and press it into the skin.

While the applicator of FIGS. 7A-7B has been depicted as placing the holder 86 slightly below the level of the ring, it will be understood that the precise position of the holder 86 in use may be adjusted as desired relative to the level of the ring.

In FIG. 7C we see the applicator of FIGS. 7A-7B provided with a reservoir 87, which may be used, for example, for liquids comprising a drug substance. In the view of FIG. 7C, the microneedle array, when attached to holder 86, has the needles pointing downward, so that if there is fluid in reservoir 87, it can flow downward to the channels in the skin created by the microneedle array. In FIG. 7D, we see a view of a portion of a microneedle array. The array has a base 180 from which microneedles such as 182 project. The base has channels such as 184 and 186 which would permit the flow of liquid from a reservoir such as 87 to the channels in the skin created by the microneedle array. Alternatively, one could have a microneedle array without the channels like 184 or 186 in which the drug substance is able to diffuse through the base of the array under conditions of use, or a microneedle array which contains or is coated with drug substance.

A reservoir such as 87 may be supplied with manual or automated equipment (e.g., pumping equipment) for causing transport of drug substance towards the skin. Automated equipment may be programmed for bolus, sustained, pulsatile, or continuous drug delivery. There may also be equipment for causing transport of a biological fluid from the skin where the microprojections have penetrated and created microchannels towards the reservoir or towards analytical equipment. Examples of such arrangements are given in U.S. Pat. No. 6,591,124.

In the applicators shown above and others of similar design, it is believed that as pressure is applied to change them from one stable state to another, the applicators hold potential energy. At the time of inversion, this potential energy is converted into a kinetic energy corresponding to the movement of the applicators during the configuration inversion. This kinetic energy is believed to cause the microneedle arrays to be pressed against the skin with a certain velocity, facilitating penetration by the microneedles.

The inversion of configuration which is characteristic of certain applicators of the invention may be achieved with manual pressure applied, for example, with the fingers. Alternatively, a tool may be provided which facilitates through leverage or otherwise the application of a pressure suitable for achieving inversion of configuration.

Figure 8:
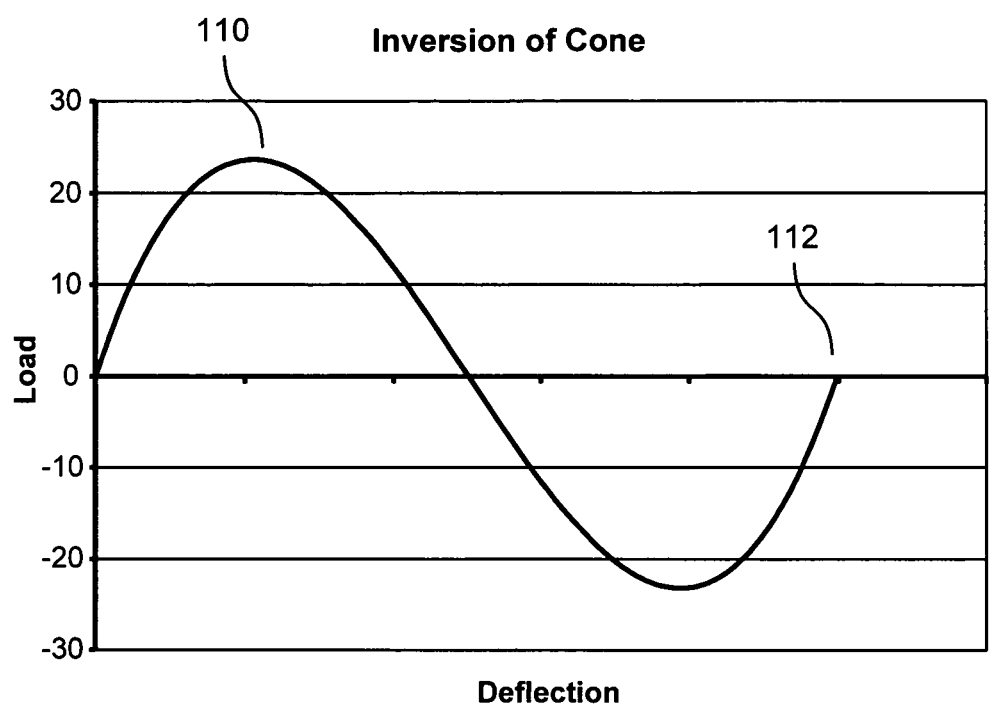

FIG. 8 depicts an approximate load-displacement curve for shape-changing applicators such as those in FIGS. 1A-1C, 2, and 16A-16B. Here the load (vertical axis) is that applied to the applicator in a generally downward direction (towards skin). The displacement (horizontal axis) is that of the central member of the applicator in a downward direction, with zero displacement indicating that the central member of the applicator is in the first stable position (that prior to use). FIG. 8 was calculated using an approximate formula for the behavior of a Belleville spring which is given in Raymond J. Roark and Warren C. Young, *Formulas for Stress and Strain* art. 10.8 (5th ed. 1975).

As may be seen in FIG. 8, initially as an increasing load is applied there is a roughly linear downward displacement of the inner portion of the applicator. A point 110 is then reached in which the applicator inverts its configuration. At this point the load may diminish and the applicator's central member will continue to move downwards. As the applicator continues downward through its configuration change, a further load becomes unnecessary to cause additional downward movement and in fact the central member of the applicator will exercise force downwards. At the rightmost portion of the graph, at maximum displacement of the central member of the applicator (point 112), a stable configuration is again reached.

There will commonly be a threshold force required to make the applicator change configuration. Such a threshold force may be between about 0.1 lbf (~0.0449 N) and about 20 lbf (~89 N), more commonly between about 1 lbf and about 10 lbf. The required force may be dependent on the size of the applicator, and thus more conveniently expressed in units of force per applicator area, for example newtons per square cm, which may range for example from about 0.01 N/cm$^2$ to 20 N/cm$^2$, more commonly 0.1 N/cm$^2$ to 10 N/cm$^2$. For the purposes of these figures, area applicator area may conveniently be measured projected on a horizontal plane.

Applicator design and force applied may affect the velocity with which the microprojection array impacts the skin. Such a velocity may be greater than about 0.01 meters per second (m/s), greater than about 0.05 m/s, about 0.1 m/s, about 0.5 m/s, or about 1 m/s. Such a velocity may be less than about 0.1 m/s, about 0.5 m/s, about 1 m/s, about 2 m/s, about 3 m/s, about 5 m/s, about 10 m/s, or about 20 m/s.

The applicators of the invention may be made of a variety of materials which possess the mechanical properties required, particularly the ability to invert configuration. Polymers believed to be suitable for the member or members which invert configuration include polyethylene terephthalate (PET), glycol-modified polyethylene terephthalate (PETG), high-impact polystyrene (HIPS), polycarbonate, polyvinylchloride (PVC), polyurethane, polyethylene, polypropylene, silicone rubber, polymethyl methacrylate (PMMA), polyvinyl alcohol (PVA), acrylonitrile-butadiene-styrene (ABS), ethylene vinyl acetate (EVA), phenylene oxide, polysulfones, or natural rubber. The member or members which invert configuration may also be made of laminates, of spring steel or similar alloys, or of composite materials, for example composite materials designed to exhibit a degree of shape memory.

The applicators may be made by a variety of techniques, such as for example vacuum forming, compression molding, injection molding, casting or stamping.

A variety of biocompatible adhesives may be used for attachment of applicators to the skin, for example acrylate adhesives, synthetic rubber adhesives, PIB (polyisobutylene) adhesives, silicone adhesives, and urethanes.

A variety of abrasives may also be used, including for example silicon carbide, aluminum oxide, diamond, cubic zirconium, garnet and cubic boron nitride.

If the microneedles are attached to the inside of the applicator, the applicator will protect the tips of the microneedles from damage during handling, shipping, storage and transport.

In the applicators shown above and others of similar design, it is believed that as pressure is applied to change them from one stable state to another, the applicators serve as a mechanical fuse. Once a threshold force is reached, the device rapidly inverts permitting the potential energy stored in the force suspended above the skin to be converted into kinetic energy. The portion of the device which holds the microneedle array may tend to impact the microneedles against the skin because the device does not invert until a threshold force is applied and because once the microneedle array holder has deflected past the outer member or members, the energy stored in the device during the application of pressure is released and accelerates the motion of the portions of the device until they reach the inverted configuration.

It may be desirable for the applicator to make a sudden noise when it inverts, since that noise provides audible positive feedback to patient or caregiver that the microneedles have been inserted. Inversion of the applicator provides in any event visual positive feedback to patient or caregiver that the microneedles have been inserted. After the applicator has inverted, the applicator may be left in place holding the microneedles in the skin so the drug has ample time to dissolve, for example if it is coated on the microneedles or contained in the microneedles. A color or transparency change may also be used to provide visual feedback in addition to or in lieu of an audible feedback.

In some uses of the applicators it may be desired to press the microneedle array one time against the skin. In other uses it may be desired to press the array into the skin a number of times, for example to deliver an active ingredient or other liquid multiple times at same or different rates to the skin through the channels created by the microneedles.

In another aspect of the present invention, a microneedle array is provided which comprises elongated members at an angle to the microneedles. The members or the attachments between them are sufficiently flexible to allow the microneedles some limited degree of motion which is perpendicular to the needles. The ends of the members which in use will be further from the skin are so arranged that they may be pressed towards the skin with the resulting pressure being transmitted to the microneedles, resulting in the microneedles being moved apart as they are pressed into the skin.

Figure 9:
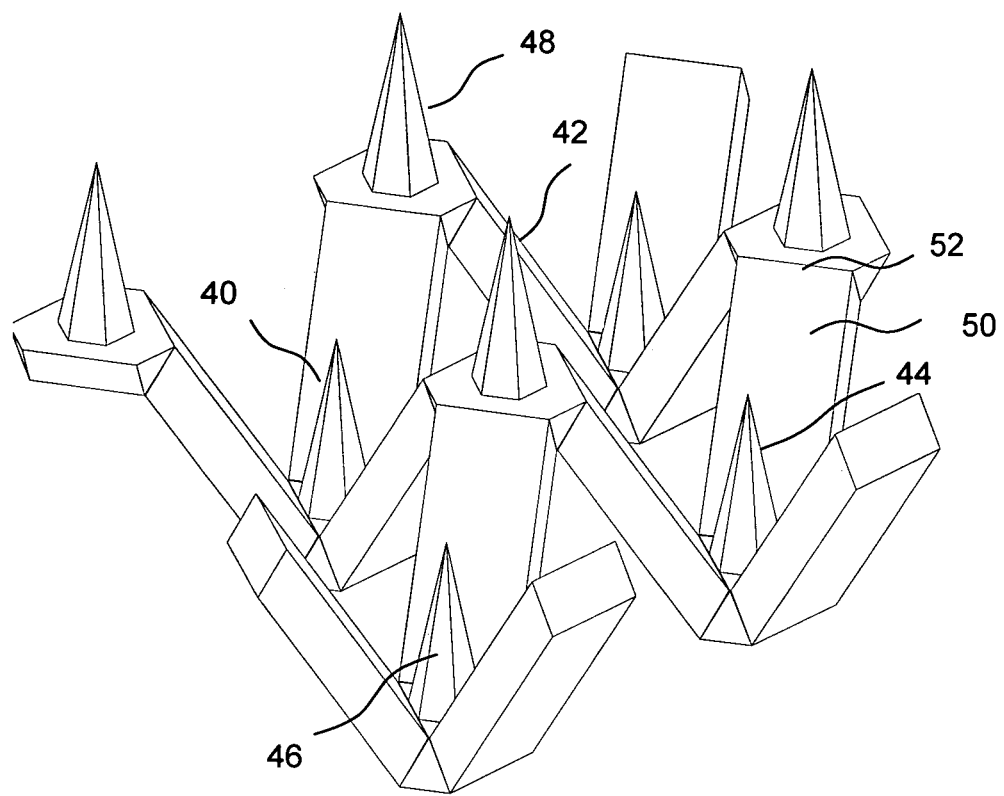

FIG. 9 depicts an exemplary embodiment of the microneedle array with elongated members at an angle to the microneedles. As may be seen in the figure, each microneedle is connected to three other microneedles. Thus, for example, microneedle 42 is connected to microneedles 40, 44, and 46. Adjacent microneedles move in paths controlled by the links relative to their adjacent microneedles.

In FIG. 9, the roughly conical microneedles are arranged such that their bottoms lie in two different planes. In the figure, microneedles 40, 44, and 46, for example, have their bottoms in the plane further from the skin, whereas microneedles 42 and 48 have their bottoms in the plane which is closer to the skin.

As may further be seen in FIG. 9, there are elongated members such as 50 which are at an angle to the microneedles. The microneedles' bases are connected to the elongated members, as at link 52.

In use, a microneedle array of the type shown in FIG. 9 would be subjected to pressure on the bases of the microneedles further away from the skin. This pressure would be transmitted to the microneedles whose bases are located in the plane closer to the skin. Those microneedles would press into the skin, penetrating it. The elongated members would also, however, expand and flatten the array as a result of that pressure, spreading the microneedles which are closer to the skin apart from each other, and thus tensioning the skin. The microneedles which are further away from the skin may then penetrate the skin.

In another embodiment related to that of FIG. 9, there may only be microneedles on the plane nearest the skin. In another embodiment the ends of the links in the plane nearest the skin may have no microneedles and may be coated with an adhesive. The microneedles are found only in the plane further from the skin. Alternatively, where the ends of the links in the plane nearest the skin have no microneedles, the needles on the plane further from the skin may extend beyond the ends of the links in the nearer plane in order to contact the skin before the nearer plane does.

Figure 10:
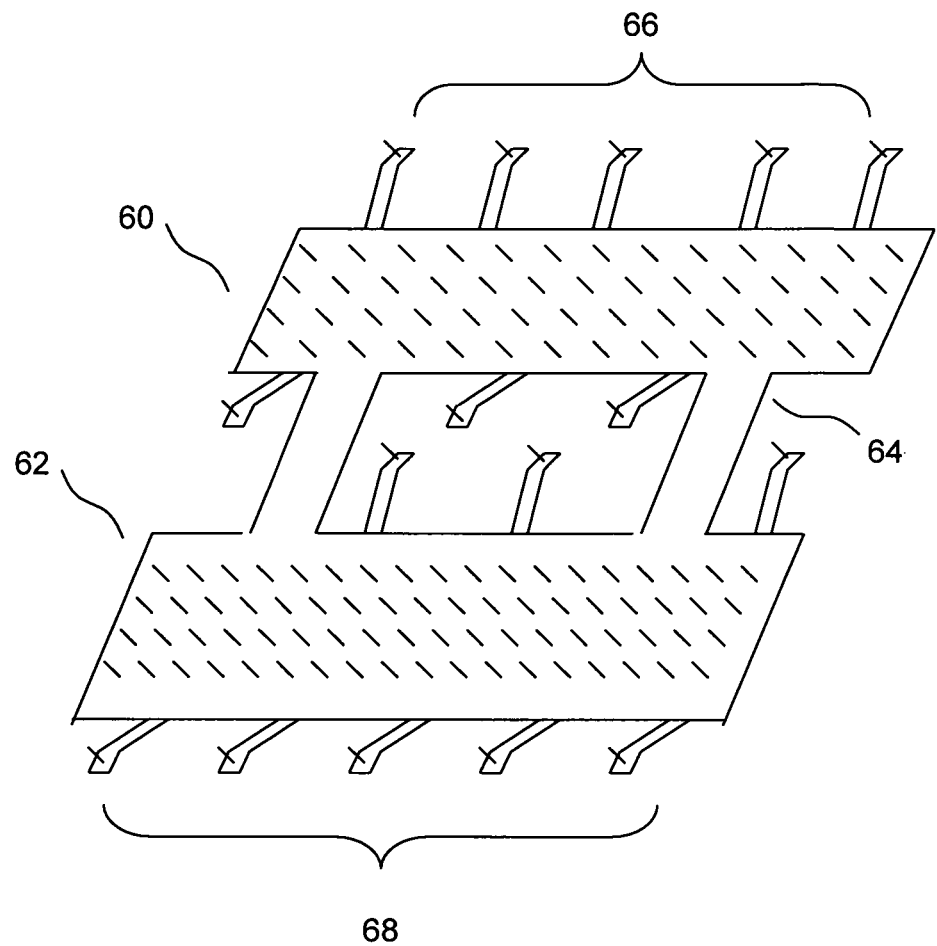

FIG. 10 schematically depicts a variation on the concept of an elongated member at an angle. In that figure one sees a microneedle array which is split into two major groups 60 and 62 of microneedles. Each major group has a base, the two bases being joined by members such as 64. From each of the bases there project elongated members such as 66 and 68, each having at least one microneedle at the end. These elongated members are flexible or flexibly attached to the bases. As a result, when the microneedle array is pressed into the skin, the first microneedles to touch the skin are those at the ends of elongated members such as 66 and 68. The flexibility or flexible coupling of these elongated members means that their ends move both into the skin and also outward away from the bases of the two groups of microneedles 60 and 62. This outward motion results in a tensioning of the skin in the area in which the bulk of the microneedles will contact, thus facilitating a greater uniformity in the permeation enhancement accomplished by those microneedles.

It will be understood by those of skill in the art that FIG. 10 is highly schematic. For example, microneedles are represented as simple straight lines, whereas of course they can have complex shapes as shown in the literature. The exact dimensions of the elongated members projecting out from the bases of the two major groups 60 and 62, and their exact angles relative to those bases, are not intended to be depicted by FIG. 10, which is not to scale.

Alternatives to FIG. 10 are possible in which, rather than dividing the bulk of the microneedles into two major groups, they are divided into more such groups each with a separate base, but with all or some of the bases connected together. A number of patterns of interconnections of the bases may be employed. The number of microneedles in each of the major groups may be more or less than the number which is schematically depicted in FIG. 10. The elongated members in FIG. 10 point in just two directions which are opposite to each other, but an array may be designed to have elongated members pointing in multiple non-collinear directions, for example pointing out at angles of 0, 90, 180, and 270 degrees with respect to some reference. The bases of the microneedle array of FIG. 10 may have, for example, holes for the passage of active ingredient. The arrays may comprise reservoirs for active agent or may be held by an applicator which contains one or more active ingredient reservoirs. The shape of the microneedles may be varied according to what is known in the art about microneedle shapes. The arrays of FIG. 10 may also be fabricated by a variety of techniques as discussed above, for example casting, molding, and embossing.

In a yet further aspect of the invention, a microneedle applicator is provided which has a member which undergoes deformation at a particular applied pressure. The use of this deformable member helps to ensure more uniform application of the microneedle array on account of the uniformity of the applied pressure achieved by providing visual feedback to the person applying the pressure or by stopping the application of the further pressure through the deformation. An exemplary embodiment is depicted schematically in FIGS. 19A-19B. The "dome" shaped member 190 in that embodiment is designed to deform at a particular reproducible applied pressure, allowing more uniform application of the microneedle array 192.

In a further aspect of the invention, an applicator may be provided which, while it does not necessarily have two stable configurations like the applicators of FIGS. 1A-1C, 2, and 3A-3B, will change shape under pressure in a way which facilitates the application of the microneedle array to skin. Such an applicator may be suitable, for example, where it is desired to apply the microneedle array once and then withdraw it. In such a situation, or in other situations, it may be convenient to maintain the pressure that changes the applicator's shape during the entire time that the microneedle array is in place penetrating the skin.

A general principle is to have projections from the microneedle array base or member that holds the microneedle array which contact skin in at least two opposite directions in an area of the projections which we may call a contact zone. The contact zone may be designed in such a way as to grasp skin easily, as for example by being coated with a pressure-sensitive adhesive. As the microneedle array base is made to approach the skin, the projections experience an outward force which causes them to push the skin outwards. A convenient arrangement is one in which these projections are arranged symmetrically about the microneedle array base. There may for example be four projections acting in four directions, or six projections acting in six directions.

Figure 11:
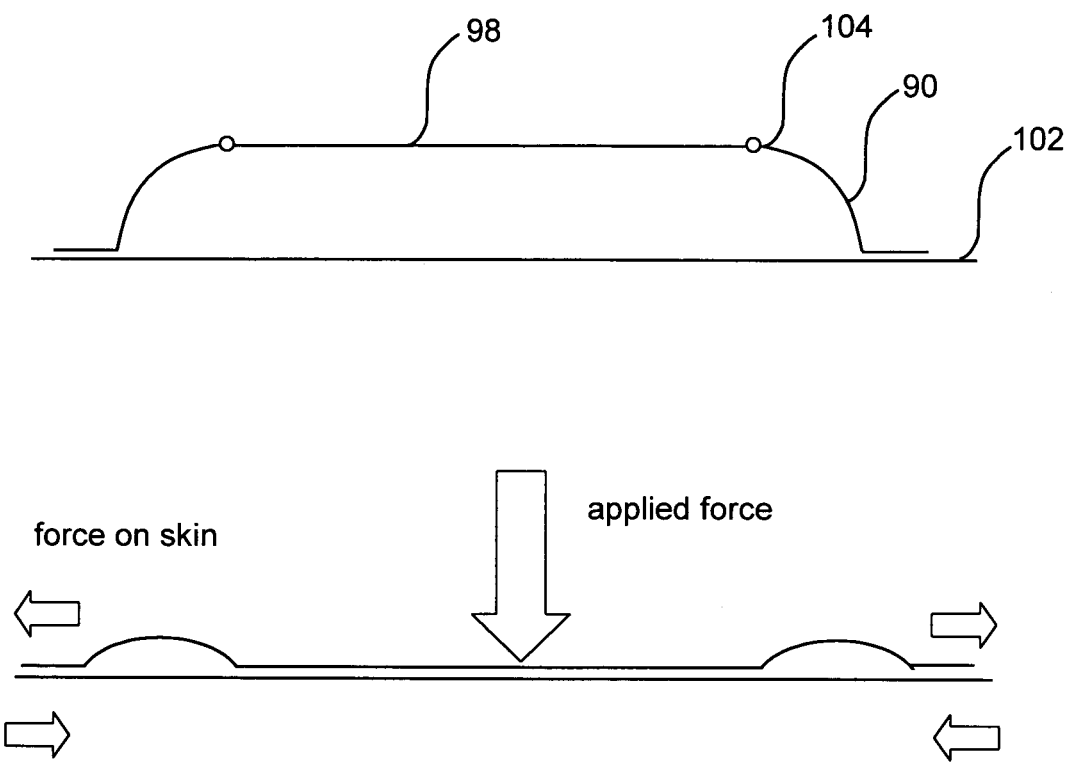

An exemplary device, depicted in schematic cross section in FIG. 11, comprises a base 98 with two or more legs such as 90 radiating from it at an angle (preferably 30 to 60 degrees) to the longitudinal axis. The legs are permitted to pivot about the points such as 104 at which they are connected to the base. The other end of each leg contacts or is connected to other components that contact the skin 102.

In use, the device of FIG. 11 is initially in the form depicted in the upper portion of that figure. The horizontal areas at the ends of the legs such as 90 are in contact with skin 102. The microneedle array is attached or integral with the base. Downward pressure is then applied. That causes the microneedle array to move towards the skin, while simultaneously causing the legs such as 90 to move outward. With suitable friction or adhesion between the horizontal ends of the legs and the skin which those horizontal ends contact, the outward movement of the device is expected to cause a tensioning of the skin.

A device along the lines of FIG. 11 may be designed in such a way that the distance between the ends of each leg can decrease once a specific force per unit length (preferably 5 to 40 g/mm, more preferably 5 to 20 g/mm, more preferably 5 to 10 g/mm) is applied along the plane of the skin. This force is measured biaxially; a particular technique for measurement is given in Example 1 below. The desirable ranges of force are believed to be such as to remove creases and redundancy from the skin without actually putting it into a range in which its strain-stress relationship is linear. Mechanisms such as curved sections, pneumatic cylinders, accordioned sections, coil springs, leaf springs or elastomer springs can be used in the legs to make them deflect or deform at a particular load.

Figure 12:
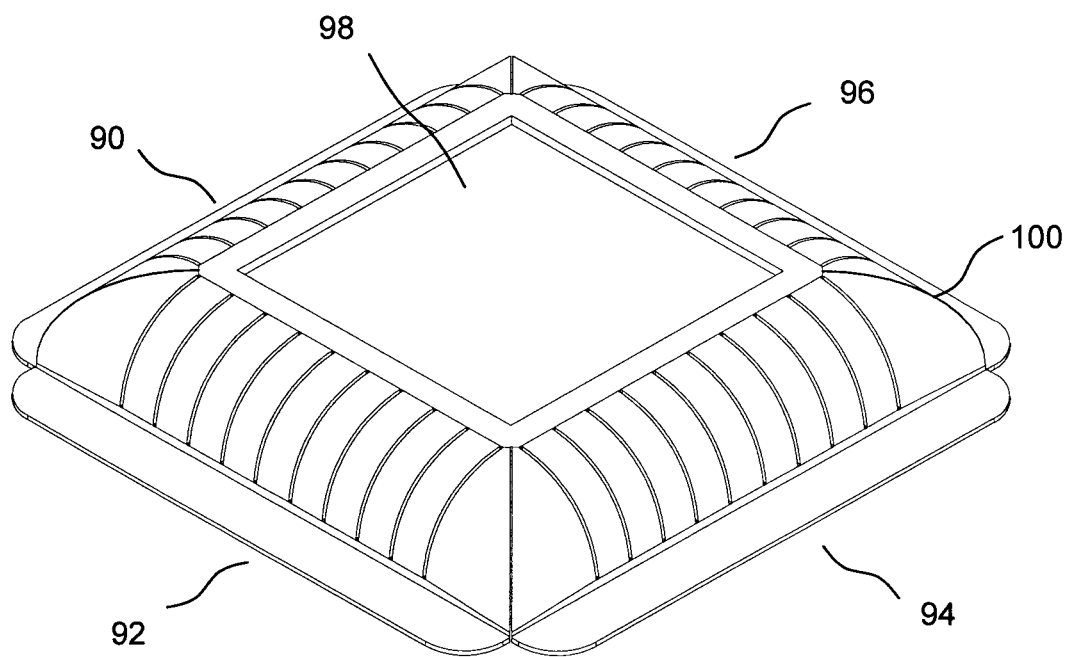
FIG. 12 depicts a particular embodiment of the concept set out in FIG. 11 in isometric view.

FIG. 12 depicts in a schematic isometric view a particular embodiment of the concept which is set out in FIG. 11. In FIG. 12 we see that there are four curved legs 90, 92, 94, and 96. Each leg has a flat area which may be adhered to skin. Pressure on the inner portion 98 of the device towards the skin causes the legs 90, 92, 94, and 96 to extend away from the center. Friction or adhesion to the skin will result in the skin being tensioned as the legs pull away. The four corners (e.g., 100) in the embodiment of FIG. 12 are slit so that they may move apart as pressure is applied to the applicator. Further, an adhesive can be added to the inner portion 98 of the device to hold it in direct contact with the skin for some period of time after downward pressure is removed.

As an alternative means of making more uniform the effect of microneedles on permeability and reducing patient-to-patient variability, a skin laminate may be used. The laminate may be stiffer than the skin and thinner than the length of the needles. The laminate may be perforated to permit the needles to pass through the holes in the laminate. Alternatively, the laminate may be continuous and the needles would penetrate it and the skin. The laminate may be a polymer film or a woven or non-woven fabric with an adhesive to attach it to the skin. The laminate may be a liquid that is applied to the skin and forms a film.

The laminate may also help to prevent microbes on the surface of the skin from entering the pathways created in the skin by the projections. Alternatively, to the extent the entry of microbes through the pathways created by microprojections is an issue, an antimicrobial active may be administered together with the active of interest. The laminate may act as reservoir of active drug substance.

The laminate may comprise, for example, polyimide-1, vinyl pyrrolidone (VP), polyvinyl pyrrolidone (PVP), a lauryl methacrylate copolymer, albumin, HPMC (hydroxypropyl methylcellulose), copolyvidone (KOLLIDON® VA 64), acrylates, cyanoacrylates, nitrocellulose, pyroxylin, polyphenylmethylsiloxane, polyethylene terephthalate, high density polyethylene, ethylene vinyl acetate, polyurethanes, or blends of polymers in these classes.

In the applicators of the invention, a wide variety of mechanisms may be employed to attach the microneedle arrays to the applicators. It is possible, for example, for the microneedle arrays to snap into position given a suitable receiving site on the applicator. Alternatively, for example, the microneedle arrays may be attached to the applicators with an adhesive. The microneedle arrays may be fabricated with protuberances suitable for facilitating the attachment of the arrays to the applicator. The microneedle arrays may be welded to the applicator.

The applicators of the invention are suitable for a wide variety of drug substances. Suitable active agents that may be administered include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In general certain drug substances (e.g., nitroglycerin) will transport readily through skin, without any special formulation requirements. Other drug substances will transport through skin with greater difficulty and, with a practical-sized system for application, only with the assistance of enhancers. Other substances are not suitable for transdermal administration even with available enhancers and thus benefit particularly from the channels which microneedles are able to produce. Such substances include, for example, peptidic or other large molecule substances for which oral administration is also not an option.

Examples of peptides and proteins which may be used with microneedle arrays are oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumour necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, parathyroid hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof.

Macromolecular active agents suitable for microneedle array administration may also include biomolecules such as antibodies, DNA, RNA, antisense oligonucleotides, ribosomes and enzyme cofactors such as biotin, oligonucleotides, plasmids, and polysaccharides. Oligonucleotides include DNA and RNA, other naturally occurring oligonucleotides, unnatural oligonucleotides, and any combinations and/or fragments thereof. Therapeutic antibodies include ORTHOCLONE OKT3® (muromonab-CD3), REOPRO® (abciximab), RITUXAN® (rituximab), ZENAPAX® (daclizumab), REMICADE® (infliximab), SIMULECT® (basiliximab), SYNAGIS® (palivizumab), HERCEPTIN® (trastuzumab), MYLOTARG® (gemtuzumab ozogamicin), CROFAB® (Crotalidae Polyvalent Immune Fab Ovine), DIGIFAB® (Digoxin Immune Fab Ovine), CAMPATH® (alemtuzumab), and ZEVALIN® (ibritumomab tiuxetan).

Microprojection arrays are advantageously used for the delivery of a variety of vaccines. These vaccines may include, for example, those approved in the United States for use against anthrax, diphtheria, hepatitis A, hepatitis B, *Haemophilus influenzae* type b, human papillomavirus, influenza, Japanese encephalitis, Lyme disease, measles, meningococcal and pneumococcal diseases, mumps, pertussis, polio, rabies, rotavirus, rubella, shingles, smallpox, tetanus, tuberculosis, typhoid, varicella, and yellow fever. The vaccines being delivered can comprise live attenuated or killed bacteria, live attenuated viruses, subunit vaccines, conjugate vaccines, synthetic vaccines, viral vectors, polysaccharide vaccines, and DNA vaccines.

Further vaccines which may be delivered by means of microprojection arrays may include vaccines (believed to be presently under development) directed against avian (pandemic) influenza virus, *Campylobacter* sp., *Chlamydia* sp.,

*Clostridium botulinum, Clostridium difficile*, dengue fever virus, *E. coli*, Ebola virus, Epstein Barr virus, nontypeable *Haemophilus influenzae*, Hepatitis C, Hepatitis E, Herpes, Herpes zoster, HIV, leishmaniasis, malaria, meningococcal serogroup B, parainfluenza, ragweed allergen, respiratory syncytial virus (RSV), Rift Valley fever virus, SARS-associated coronavirus, *Shigella* sp., *Staphylococcus aureus, Streptococcus* Group A (GAS), *Streptococcus* Group B (GBS), tick-borne encephalitis, Venezuelan equine encephalitis, and West Nile virus.

A wide variety of mechanisms may be used to provide and apply the drug substance. For example, the drug substance may be coated onto the microneedle arrays. It may be placed in a reservoir from which the drug substance travels to the skin, for example, through the base of the microneedle array, e.g., via small channels formed in the base. The drug reservoir may be part of a button used in pressing the microneedle array against the skin.

Fluid pressure may be used, for example, to cause the drug substance to travel from the reservoir. Such fluid pressure may be generated by manual or finger pressure against a flexible wall enclosing the reservoir. The fluid pressure may be generated by a gas-forming chemical reaction in an enclosed area. The fluid pressure may alternatively be generated by a pump such as a bulb pump used, for example, when measuring blood pressure, or an electrically operated pump. Alternatively, an external source of compressed air or other compressed fluid may be used to provide a fluid pressure which serves to cause the drug substance to travel from the reservoir to the skin. Iontophoresis and electroosmosis, briefly described below, may also be employed to transport the drug substance to the skin where it may further penetrate by means of the channels created by the microneedle arrays.

With suitable microneedle arrays made of appropriate materials, the drug substance may be dissolved or suspended in the microneedles themselves. The drug substance may also be in solid form, for example as a powder, and may during the process of use be mixed with a suitable liquid for transmission to the body.

Where a reservoir is used to store the drug substance, the reservoir may be made of a wide variety of materials. It may, for example, simply be an enclosed area in which the drug substance is stored in a suitable liquid solution. The solution may, for example, be designed to facilitate absorption under the circumstances of the administration with partial, potentially healing channels existing in the skin. The reservoir may alternatively be a polymeric matrix within which the drug substance is located and from which it may diffuse outwards and towards the skin. Instead of a polymeric matrix, the reservoir could for example comprise a nonwoven material or material of small dimensions onto which a solution comprising the drug substance may adsorb. The reservoir may also encompass, for example, a hydrogel.

In addition to the drug substance, it may be intended that other substances be included in a reservoir together with the drug substance and potentially transport into skin with the active drug substance. Such substances may be, for example, permeation enhancers. Information about permeation enhancers may be found, for example, in Tapash K. Ghosh et al., *Transdermal and Topical Drug Delivery Systems* chapter 11 (Interpharm Press 1997).

Exemplary permeation enhancers include, by way of illustration and not limitation, sulfoxides such as dimethylsulfoxide and decylmethylsulfoxide; ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), TWEEN® (20, 40, 60, 80) (polysorbates) and lecithin; the 1-substituted azacycloheptan-2-ones, particularly 1-n-dodecylcyclazacycloheptan-2-one; alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid; and mixtures thereof.

Wetting agents and viscosity modifiers may also be included in the formulation of the drug substance and/or the microneedle array itself. Exemplary wetting agents include sodium dodecyl sulfate, TWEEN® in various grades, sorbitans, laureths, polyoxethylene monostearates, glyceryl triacetate, and PLURONICS® (poloxamers) in various grades. Exemplary viscosity modifies include cellulose derived polymers and sugars.

Other substances to be administered together with the drug substance may include compositions designed to retard the healing of the channels created in the skin by the microneedles. Certain compositions indicated to have that effect are disclosed in U.S. Published Patent Application No. 2002/0102292.

The drug substance may be formulated in a variety of other ways for administration through a microneedle array. The pH of the formulation may be controlled, as for example with glycerol buffers, citrate buffers, borate buffers, phosphate buffers or citric acid-phosphate buffers. It may be found convenient, for example, to include a component in the formulation which facilitates the wetting of the microneedle array by a liquid solution comprising the drug substance.

The formulation may also include agents commonly employed to prolong the shelf life of pharmaceutical preparations. For example, antimicrobial agents may be employed. Suitable antimicrobial agents are typically selected from the group consisting of the methyl and propyl esters of p-hydroxybenzoic acid (i.e., methyl and propyl paraben), sodium benzoate, sorbic acid, imidurea, proteins (i.e., lysozyme), silver salts, and combinations thereof.

Agents employed to protect the formulation against degradation may also include, for example, antioxidants such as primary antioxidants which are peroxy free radical scavengers and secondary antioxidants which induce decomposition of hydroperoxides, and thus protect a material from degradation by hydroperoxides. Examples of primary antioxidants are tetrakis [methylene (3,5-di-tert-butyl-4-hydroxyhydrocinnamate)]methane (e.g., IRGANOX®1010, from Ciba-Geigy Corp., Hawthorne, N.Y.) and 1,3,5-trimethyl-2,4,6-tris [3,5-di-t-butyl-4-hydroxy-benzyl]benzene (e.g., ETHANOX®330, from Ethyl Corp.). Examples of secondary antioxidants include tris(2,4-di-tert-butylphenyl)phosphite (e.g., IRGAFOS®168, Ciba-Geigy Corp.). Other suitable antioxidants include, for example, ascorbic acid, ascorbic palmitate, tocopherol acetate, propyl gallate, butylhydroxyanisole, butylated hydroxytoluene, IRGANOX®E17 (Ciba-Geigy), IRGANOX®1520 D (Ciba-Geigy), bis(1,2,2,6,6-pentamethyl-4-piperidinyl)-(3,5-di-tert-butyl-4-hydroxybenzyl)butylpropanedioate, (available as TINUVIN®144 from Ciba-Geigy Corp.) or a combination of octadecyl 3,5-di-tert-butyl-4-hydroxyhydrocinnamate (also known as octadecyl 3-(3',5'- di-tert-butyl-4'-hydroxyphenyl)propionate) (available as NAUGARD®76 from Uniroyal Chemical Co., Middlebury, Conn.) and bis(1,2,2,6,6-pentamethyl-4-piperidinylsebacate) (available as TINUVIN®765 from Ciba-Geigy Corp.).

While reference has been made here to a drug substance, naturally there is nothing to prevent the use of a microneedle array with an applicator of the invention for cotherapy in which two or more drug substances are simultaneously or concurrently administered, or administered one after the other.

An applicator of the invention may advantageously be combined, for example, with an arrangement to vibrate the microneedle array in order to facilitate insertion. The array may be vibrated, for example, manually, or with the aid of a manually activated vibrating device, for example one operating on the principle of the tuning fork. The microneedle array may be vibrated by means of an electric motor, or (usually at a higher frequency such as an ultrasound frequency) by means of a piezoelectric transducer which may be coupled to either the applicator or the array itself. The vibration may take place during the process of microneedle array insertion, or alternatively the vibration may take place occasionally or episodically after the microneedle array has been inserted, in order to improve the flow characteristics of the channels created by the array, for example when a temporary boost in the rate of transport of drug substance is desired.

The applicators of the invention may also be designed for use in iontophoresis. Iontophoresis is a well-known noninvasive technique that may be used to deliver a compound of interest to, or to extract a compound of interest from, a body tissue of a patient. In practice, two iontophoretic electrodes are placed on a body tissue, typically the skin or mucosa, in order to complete an electrical circuit. At least one of the electrodes is considered to be an active iontophoretic electrode, while the other may be considered as a return, inactive, or indifferent electrode. The compound of interest is transported at the active electrode across the tissue as a permeant when a current is applied to the electrodes through the tissue. Compound transport may occur as a result of a direct electrical field effect (e.g., electrophoresis), an indirect electrical field effect (e.g., electroosmosis), electrically induced pore or transport pathway formation (electroporation), or a combination of any of the foregoing.

It may be that the applicators of the invention are packaged together with a microneedle array and associated reservoir to form a kit comprising at least an applicator and an array. Alternatively, the applicator may be a separate and reusable entity into which a number of microneedle arrays and reservoirs are inserted one after another for application. In such circumstances it may be desired that there be a fixed procedure for sterilizing the applicator between uses, for example autoclaving or washing in a sterile bactericidal liquid.

A kit may be designed to maintain the array, or the array and the applicator, sterile. A sterility may be desired which is comparable to that specified for parenteral dosage forms. Advantageously the packaging for the kit components could be constructed from flexible polyvinylchloride or polyolefin thermoplastics of the type used for packaging substantial volumes of intravenous solution. The array and/or applicator could also be packaged, for example, in sterile stoppered glass, in a laminated foil pouch, or in plastic containers. Reference is made to *Remington: the Science and Practice of Pharmacy* (20th ed., Alfonso R. Gennaro ed., Lippincott Williams & Wilkins 2000), chapters 40 and 41, for further information about the formulation of sterile dosage forms and their packages.

If an applicator changes configuration and is intended for use with multiple microneedle arrays, it is desirable that the applicator be able to move back and forth from one configuration to another repeatedly without degradation, for example a minimum of about 2 times, about 10 times, about 50 times, or about 100 times.

Example 1

To control the force in the plane of the skin to desirable values it is helpful to be able to measure forces which an applicator of a particular design is exerting. A convenient methodology is as follows.

Figure 13:
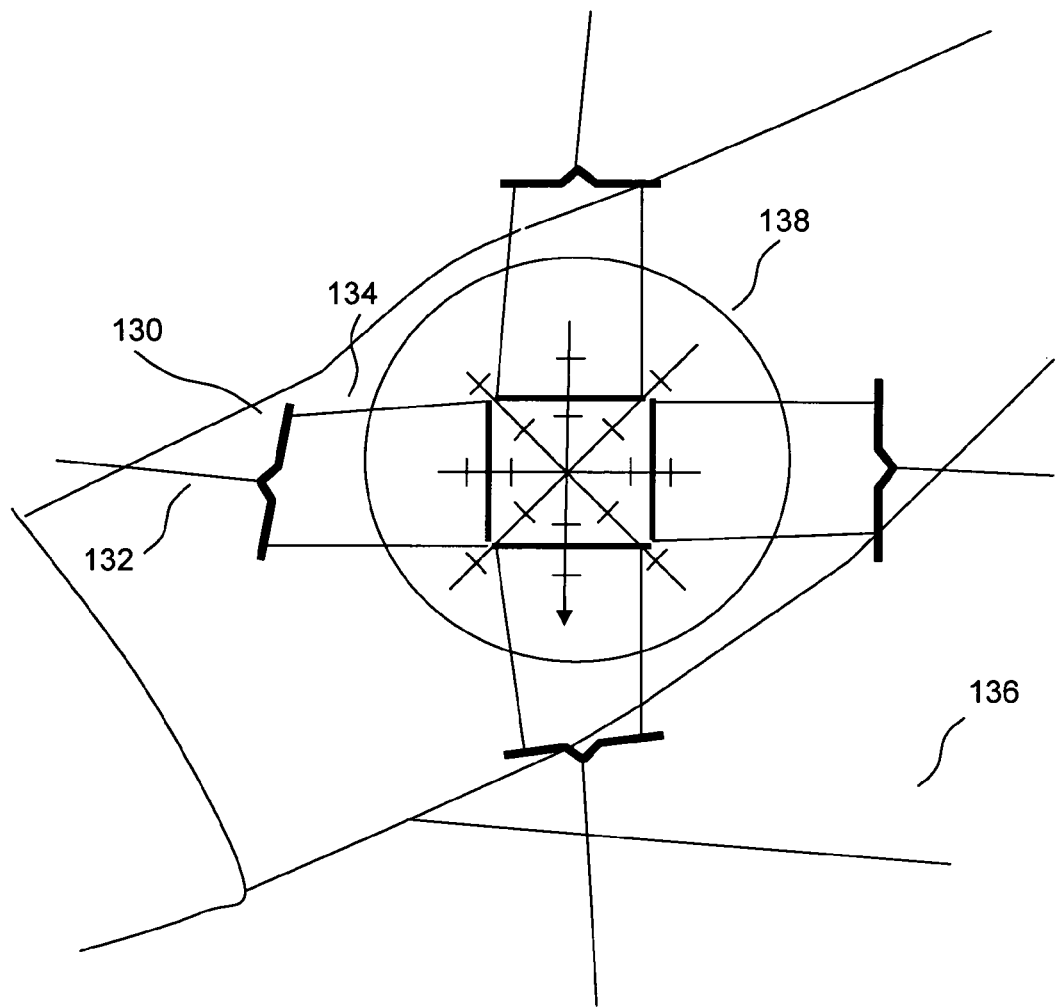
FIG. 13 depicts an arrangement for tensioning skin biaxially in a controlled manner.

A mechanism is constructed for exercising a controlled force in a biaxial way along four perpendicular directions. Such a mechanism is depicted in FIG. 13. Four small metal cylinders such as 130 are attached through strings such as 132 to weights (not shown). The cylinders are also attached to thin polymeric films such as 134, which are in turn attached (e.g., via an adhesive) to the skin of a human subject. The weights serve to provide a controllable tension which is biaxial. A transparent overlay 138 is used to more easily measure strain. A base 136 is provided to hold the subject's arm and to guide (for example with pulleys) the strings such as 132 which connect the metal cylinders such as 130 to the weights.

Figure 14:
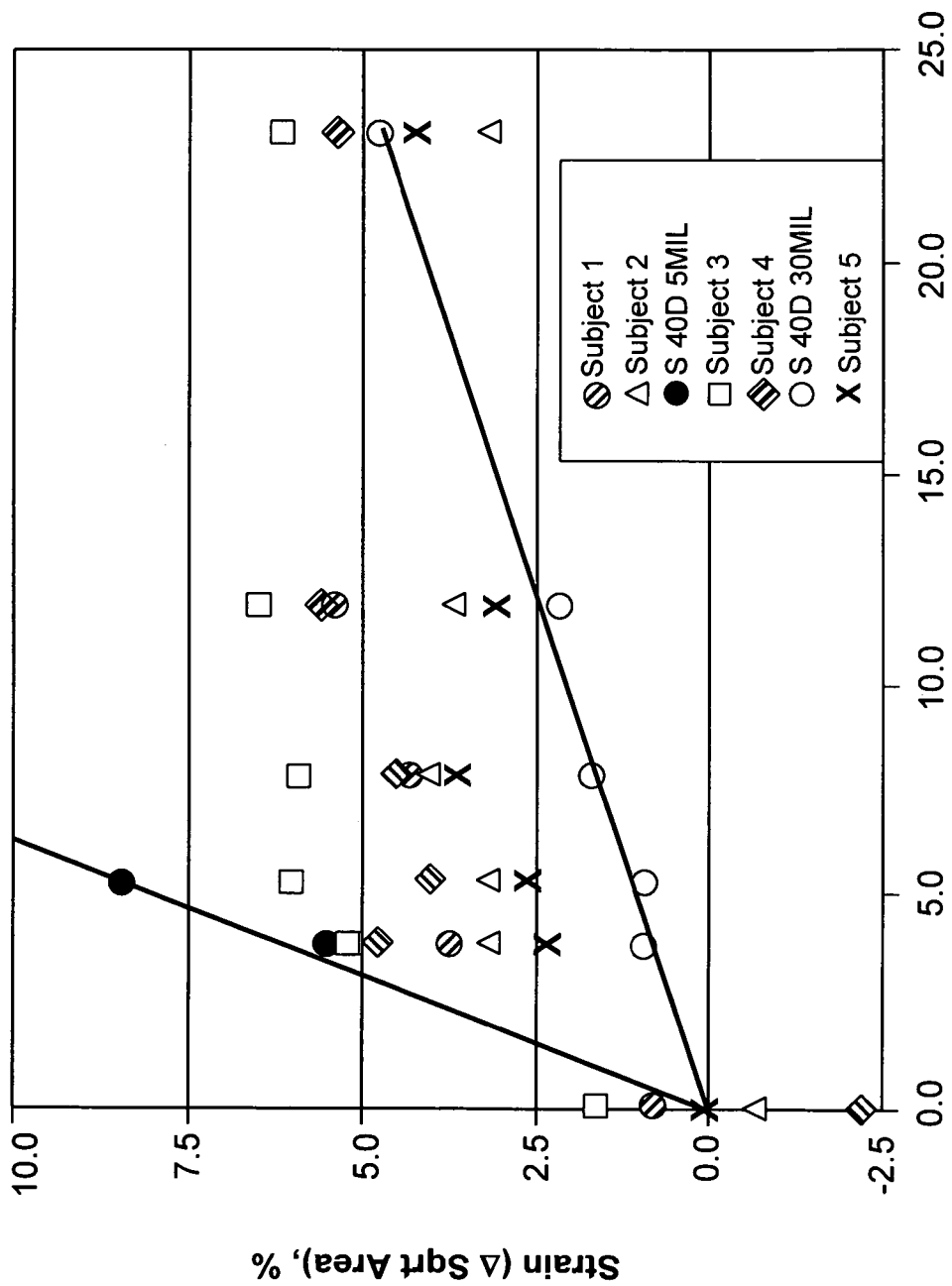
FIG. 14 depicts the biaxial strain-stress curves for five human subjects and two thicknesses of silicone rubber, 5 mils and 30 mils.

Using an apparatus like that in FIG. 13, stress-strain curves were measured for five human subjects, giving the results depicted in FIG. 14. Strain is calculated using the change in the square root of the area of the specimen, i.e., as (sqrt(final area)−sqrt(initial area))/sqrt(initial area). The figure gives an idea of the variability in the strain-stress curve for human skin.

Strain-stress curves were also measured for two thicknesses of silicone rubber. The purpose of this measurement was to correlate the silicone rubber stress-strain curve with that of the human subjects in order to use the silicone rubber as a test bed for different shapes of applicators. The applicator is applied to silicone rubber as if it were human skin. The force exerted by the applicator may be estimated from the strain which it causes on the silicone rubber.

The stress-strain curves of FIG. 14 may be compared with the generalized human skin strain-stress curve of FIG. 15, which is taken from G. L. Wilkes et al., "The biomechanical properties of skin," *CRC Critical Reviews in Bioengineering,* 1:453-495 (1973). The curves of FIG. 14 tend to correspond to the bottom part of the generalized curve of FIG. 15, approximately in the portion of that figure which is labeled Phase 2. This may be a desirable area of the strain-stress curve in which to operate for purposes of applying microneedle arrays.

It is to be understood that while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

We claim:

1. An applicator for a microprojection array, comprising:
   an inner portion and an outer portion that is concentric to and integral with the inner portion;
   a contact zone on the outer portion for contacting skin at an application site;
   a region on the inner portion to which a microprojection array can be attached;
   wherein upon application of force to the inner portion, the applicator is deformable from a first configuration to a second configuration in which the applicator stably remains until a further force is applied to the applicator,
   wherein the microprojection array contacts the application site when the applicator is in the second configuration; and
   wherein the applicator, when placed adjacent skin at the application site in its first configuration, has a shape such that the outer portion slopes towards the skin such that the contact zone is capable of contacting the skin, and the applicator has a shape in its second configuration wherein the outer portion extends away from the skin such that the contact zone is no longer in skin contact.

2. The applicator of claim 1, wherein at least a portion of the contact zone is coated with adhesive.

3. The applicator of claim 1, wherein the inner and outer portions meet at a closed curve.

4. The applicator of claim 3, wherein the curve at which the inner and outer portions meet is approximately circular.

5. The applicator of claim 1, wherein the applicator deforms between the first and second configurations with manual pressure.

6. The applicator of claim 5, wherein the applicator can be deformed between the first and second configurations at least 10 times without damage to the applicator.

7. The applicator of claim 1, wherein the applicator is deformable between the first and second configurations at least 2 times without damage to the applicator.

8. The applicator of claim 1, wherein the inner portion or the outer portion or both comprise a polymer selected from the group consisting of polyethylene terephthalate, glycol-modified polyethylene terephthalate, high-impact polystyrene, polycarbonate, polyvinylchloride, polyurethane, polyethylene, polypropylene, silicone rubber, polymethyl methacrylate, polyvinyl alcohol, acrylonitrile-butadiene-styrene, ethylene vinyl acetate, phenylene oxide, polysulfones, and natural rubber.

9. The applicator of claim 1, wherein the inner portion or the outer portion or both comprise a metal.

10. The applicator of claim 1, further comprising a further structure capable of mating with or attaching to the inner portion, wherein pressure in a direction approximately perpendicular to the inner portion which is applied to the further structure is spread more uniformly to the inner and outer portions of the applicator than pressure applied directly to the inner portion.

11. The applicator of claim 10, wherein the further structure has approximately the shape of the inner and outer portions in the first stable configuration.

12. The applicator of claim 10, wherein as the applicator approaches the second stable configuration, the outer portion of the applicator presses against the further structure and is held in position by the further structure.

13. The applicator of claim 1, wherein the inner portion of the applicator is approximately flat and the outer portion is approximately frustoconical.

14. The applicator of claim 1, wherein the inner portion has a shape which projects towards the skin when the applicator is used.

15. The applicator of claim 1, wherein the portion of the applicator not including the microprojections is symmetric under rotation about an axis which is approximately parallel to a microprojection.

16. The applicator of claim 1, wherein the outer perimeter of the contact zone does not significantly expand when the applicator shifts between the first and second stable configurations.

17. A method for testing for a condition in a patient, comprising:
   (a) applying a microprojection array to the skin of the patient employing an applicator as described in claim 1,
   (b) collecting biological fluid using microchannels created in the skin by the microprojection array, and
   (c) detecting the presence of one or more biomarkers in the collected biological fluid.

18. A method for administering an active agent, comprising:
   (a) applying a microprojection array to the skin of the patient employing an applicator as described in claim 1, and
   (b) causing the active agent to pass through skin using microchannels created in the skin by the microprojection array.

19. The method of claim 18, wherein the microprojection array is used for one of bolus, sustained, pulsatile, or continuous drug delivery.

20. The method of claim 18, wherein the microprojection array is used for one of acute, intermittent, or chronic drug delivery.

21. The method of claim 18, wherein the active agent has a molecular weight exceeding 500 Daltons.

22. The method of claim 21, wherein the active agent has a molecular weight exceeding 1000 Daltons.

23. The method of claim 18, further comprising the step of applying an adhesive to skin and then contacting the applicator to the adhesive applied to skin.

24. The method of claim 18, wherein an adhesive is applied to the outer portion of the applicator prior to applying the microprojection array to the skin.

25. An applicator for a microprojection array, comprising:
   an inner and outer portion wherein
   (a) the inner portion comprises a region for attaching a microprojection array,
   (b) the outer portion comprises a contact zone designed for contacting skin at an application site, and
   (c) the relative positions of the inner and outer portions can be varied by application of force to the inner portion between a first stable configuration and a second configuration in which (i) the applicator remains until a further force is applied to return it to the first stable configuration, and (ii) the outer portion in the second stable configuration is inverted about the contact zone with respect to the first stable configuration, such that the outer portion and the contact zone extend at an angle away from the skin at the application site;
   wherein the microprojection array contacts the application site when the applicator is in the second configuration.

26. The applicator of claim 25, wherein the applicator comprises a laminate at least one of whose components contributes energy to the transition of the applicator to the second configuration.

27. The applicator of claim 25, wherein the inner portion comprises an inner contact zone, further comprising an adhesive on the inner contact zone.

28. An applicator for a microprojection array comprising an inner and outer portion wherein
   (a) the microprojection array attaches to or is integral with the inner portion,
   (b) the outer portion has a contact zone designed for contacting skin at an application site,
   (c) the inner and outer portions are integral with each other, and
   (d) the relative positions of the inner and outer portions may be varied between a first and a second configuration, wherein the outer portion in the second stable configuration is inverted about the contact zone with respect to the first stable configuration in the absence of an adhesive, such that the outer portion and the contact zone extend at an angle away from the skin at the application site.

* * * * *